(12) United States Patent
Murphy et al.

(10) Patent No.: US 6,399,785 B1
(45) Date of Patent: Jun. 4, 2002

(54) MULTIPLY-SUBSTITUTED FULLERENES

(75) Inventors: Randall B. Murphy, Irvington, NY (US); Stephen R. Wilson, Chatham; Quing Lu, Livingston, both of NJ (US)

(73) Assignee: C-Sixty, Inc., Toronto (CA)

( * ) Notice: Subject to any disclaimer, the term of this patent is extended or adjusted under 35 U.S.C. 154(b) by 0 days.

(21) Appl. No.: 09/702,143

(22) Filed: Oct. 30, 2000

Related U.S. Application Data

(63) Continuation of application No. 08/969,261, filed on Dec. 23, 1998, now Pat. No. 6,162,926, which is a continuation of application No. 08/509,209, filed on Jul. 13, 1995, now abandoned.

(51) Int. Cl.$^7$ .................... C07D 403/04; C07D 403/14; C07D 437/02

(52) U.S. Cl. ...................... 548/417; 548/460; 549/416; 549/432; 549/439; 556/482; 558/388; 560/8; 560/124; 568/303; 568/308; 568/579; 568/630; 568/632; 568/808

(58) Field of Search .............................. 558/388; 560/8, 560/124; 548/417, 460; 556/482; 568/303, 308, 579, 630, 632, 808; 549/416, 432, 434

(56) References Cited

U.S. PATENT DOCUMENTS

| | | | |
|---|---|---|---|
| 5,177,248 A | 1/1993 | Chiang et al., I | 560/86 |
| 5,294,732 A | 3/1994 | Chiang et al., II | 560/86 |
| 5,382,718 A | 1/1995 | Bekiarian et al. | 570/129 |
| 5,386,048 A | 1/1995 | West et al. | 556/430 |
| 6,162,926 A | 12/2000 | Randall et al. | 548/417 |

FOREIGN PATENT DOCUMENTS

| | | | |
|---|---|---|---|
| WO | WO 94/00552 | 1/1994 | 560/86 |

OTHER PUBLICATIONS

Akasaka, T., et al., "Adduct of $C_{70}$ at the Equatorial Belt: Photochemical Cycloaddition with Disilirane," *J. Am. Chem. Soc.*, (1994), 116:2627–2628.

Averdung, J., et al., "Photoreaktionen mit Fulleren–$C_{60}$ [3+2]–Photocyloaddition von 2,3–Diphenyl–2H–azirin," *Chem. Ber.*, (1994), 127:787–789.

Balch, A.L., et al., "Directing Effects in a Fullerene Epoxide Addition. Formation and Structural Characterization of $(\eta^2-C_{60}O)Ir(CO)Cl(P(C_6H_5)_3)_2$," *Inorg. Chem.*, (1994), 33:2071–2072.

Barbas, III, C.F., et al., "Direct selection of antibodies that coordinate metals from semisynthetic combinatorial libraries," *Proc. Natl. Acad. Sci.*, (1993), 90:6385–6389.

Baum, R.M., "Combinatorial Approaches Provide Fresh Leads for Medicinal Chemistry," *C&EN*, (1994), 20–26.

Bensasson, R.V., "$C_{60}$ in Model Biological Systems. A visible–UV Absorption Study of Solvent–Dependent Parameters and Solute Aggregation," *J. Phys. Chem.*, (1994), 98:3492–3500.

Bohacek, R.S., et al., "Multiple Highly Diverse Structures Complementary to Enzyme Binding Sites: Results of Extensive Application of a de Novo Design Method Incorporating Combinatorial Growth," *J. Am. Chem. Soc.*, (1994), 116:5560–5571.

Borchardt, A., et al., "Synthetic Receptor Binding Elucidated with an Encoded Combinatorial Library," *J. Am. Chem. Soc.*, (1994), 116:373–374.

Boyce, R., et al., "Peptidosteroidal Receptors for Opioid Peptides. Sequence–Selective Binding Using a Synthetic Receptor Library," *J. Am. Chem. Soc.*, (1994), 116:7955–7956.

Carell, T., et al., "A Novel Procedure for the Synthesis of Libraries Containing Small Organic Molecules," *Angew. Chem. Int. Ed. Engl.*, (1994) 33:2005–2009.

Caron, C., et al., "Selective Electrosynthesis of $(CH_3)_2C_{60}$: A Novel Method for the Controlled Functionalization of Fullerenes," *J. Am. Chem. Soc.*, (1993), 115:8505–8506.

Chen, J.K., et al., "Biased Combinatorial Libraries: Novel Ligands for the SH3 Domain of Phosphatidylinositol 3–Kinase," *J. Am. Chem. Soc.*, (1993), 115:12591–12592.

Chen, J.Y.C., et al., "Catalytic Antibodies from Combinatorial Libraries," *J. Am. Chem. Soc.*, (1993), 115:357–358.

Chiang, L.Y., et al., "Multi–hydroxy Additions onto $C_{60}$ Fullerene Molecules," *J. Chem. Soc. Chem. Commun.*, (1992), 1791–1793.

Dooley, C.T., et al., "Acetalins: Opioid receptor antagonists determined through the use of synthetic peptide combinatorial libraries," *Proc. Natl. Acad. Sci.*, (1993), 90:10811–10815.

Dooley, C.T., et al., "The Use of Positional Scanning Synthetic Peptide Combinatorial Libraries for the Rapid Determination of Opioid Receptor Ligands," *Life Sciences*, (1993), 52:1509–1517.

Elemes, Y., et al., "Reaction of $C_{60}$ with Dimethyldioxirane–Formation of an Epoxide and a 1,3–Dioxolane Derivative," *Angew. Chem. Intl. Ed. Engl.*, (1992), 31:351–353.

(List continued on next page.)

Primary Examiner—Floyd D. Higel
(74) Attorney, Agent, or Firm—Barry Evans, Esq.; Kramer Levin Naftalis & Frankel, LLP

(57) ABSTRACT

The invention is directed to multiply-substituted fullerene derivatives of novel configurations, and methods for their preparation and use. The methods involve the combinatorial synthesis of a library of fullerene derivatives and comprises the steps of forming a mixture of fullerene derivatives by reacting the $C_n$ fullerene with two or more reactive precursor compounds, and removing the unreacted compounds to yield the fullerene derivatives having the desired activity. Methods for the identification and screening of a combinatorial library of fullerenes by $^3$He-nuclear magnetic resonance and electrospray mass spectrometry to define members with the optimal desired activity are also provided.

1 Claim, 9 Drawing Sheets

OTHER PUBLICATIONS

Fagan, P.J., et al., "The Chemical Nature of Buckminsterfullerene ($C_{60}$) and the Characterization of a Platinum Derivative," *Science*, (1991), 252:1160–1161.

Fagan, P.J., et al., "Synthesis, Chemistry, and Properties of a Monoalkylated Buckminsterfullerene Derivative, t–$BuC_{60}$ Anion," *J. Am. Chem. Soc.*, (1992), 114:9697–9699.

Gallop, M.A., et al., "Applications of Combinatorial Technologies to Drug Discovery. 1. Background and Peptide Combinatorial Libraries," *Journal of Medicinal Chemistry*, (1994), 37:1233–1251.

Gordon, E.M., et al., "Applications of Combinatorial Technologies to Drug Discovery. 2. Combinatorial Organic Synthesis, Library Screening Strategies, and Future Directions," *Journal of Medicinal Chemistry*, (1994), 37:1385–1401.

Hawker, C.J., et al., "The Synthesis and Characterization of a Self–Assembling Amphiphilic Fullerene," *J. Org. Chem.*, (1994), 59:3503–3505.

Hawkins, J.M., et al., "Regiochemistry of the Bisosmylation of $C_{60}$: "Ortho, Meta, and Para" in Three Dimensions," *J. Am. Chem. Soc.*, (1992), 114:7954–7955.

Hirsch, A., et al., "Fullerene Chemistry in Three Dimensions: Isolation of Seven Regioisomeric Bisadducts and Chiral Trisadducts of $C_{60}$ and Di(ethoxycarbonyl)methylene," *Angew. Chem. Int. Ed. Engl.*, (1994), 33:437–438.

Hirsch, A., et al., "Regiochemistry of Multiple Additions to the Fullerene Core: Synthesis of a T$\eta$–Symmetric Hexakisadduct of $C_{60}$ with Bis(ethoxycarbonyl)methylene," *J. Am. Chem. Soc.*, (1994), 116:9385–9386.

Hoke, II, S.H., et al., "Reaction of Fullerenes and Benzyne," *J. Org. Chem.*, (1992), 57:5069–5071.

Ishida, T., et al., "Fullerene Aziridine. Facile Synthesis and Spectral Characterization of Fullerene Urethane, $C_{60}NCO_2CH_2CH_3$," *Chemistry Letters*, (1994), 561–562.

Iyoda, M., et al., "Synthesis and Properties of a Novel Redox System containing Fullerene and p–Benzoquinone," *J. Chem. Soc., Chem. Commun.*, (1994), 1929–1930.

Kaganovskii, Yu. S., et al., "Langmuir–Blodgett films of the fullerene $C_{60}$," *JETP Lett.*, (1994), 60:370–374.

Kikuchi, K., et al., "Encapsulation of Radioactive [159]Gd and [161]Tb Atoms in Fullerene Cages," *J. Am. Chem. Soc.*, (1994), 116:9775–9776.

Komatsu, K., et al., "Ene Reaction as a New Method for Functionalization of Fullerene $C_{60}$," *Chemistry Letters*, (1994), 635–636.

Komatsu, K., et al., "Reaction of $C_{60}$ with Chlorophenyldiazirine. Spectral and Electronic Properties of the $C_{60}$–Chlorophenylcarbene 1:1 Adduct," *Chemistry Letters*, (1993), 2163–2166.

Maggini, M., et al., "Addition of Azomethine Ylides to $C_{60}$: Snythesis, Characterization, and Functinalization of Fullerene Pyrrolidines," *J. Am. Chem. Soc.*, (1993), 115:9798–9799.

Maggini, M., et al., "Synthesis of N–Acylated Fulleropyrrolidines: New Materials for the Preparation of Langmuir–Blodgett Films Containing Fullerenes," *Tetrahedron Letters*, (1994), 35:2985–2988.

Morton, J.R., et al., "The Dimerization of $RC_{60}$ Radicals," *J. Am. Chem. Soc.*, (1992), 114:5454–5455.

Muthu, S., et al., "Reaction of Buckminsterfullerene with 1,3–Diphenylnitrilimine: Synthesis of Pyrazoline Derivatives of Fullerene," *Tetrahedron Letters*, (1994), 35:1763–1766.

Naim, A., et al., "Reversible Addition of Hydroxide to the Fullerenes," *Tetrahedron Letters*, (1992), 33:7097–7100.

Nelson, M.A., "Effects of Acute and Subchronic Exposure of Topically Applied Fullerene Extracts on the Mouse Skin," *Toxicology and Industrial Health*, (1993), 9:623–630.

Olah, G.A., et al., "Chlorination and Bromination of Fullerenes. Nucleophilic Methoxylation of Polychlorofullerenes and Their Aluminum Trichloride Catalyzed Friedel–Crafts Reaction with Aromatics to Polyarylfullerenes," *J. Am. Chem. Soc.*, (1991), 113:9385–9387.

Olah, G.A., et al., "Polyarenefullerenes, $C_{60}$(H–Ar)$\eta$ Obtained by Acid–Catalyzed Fullerenation of Aromatics," *J. Am. Chem. Soc.*, (1991), 113:9387–9388.

Orfanopoulos, M. et al., "Fullerene $C_{60}$ and $C_{70}$ Photosensitized Oxygenation of Olefins," *Tetrahedron Letters*, (1994), 35:1945–1948.

Osterodt, J., et al., "Verkronte Fullerene," *Chem. Ber.*, (1993), 126:2331–2336.

Pavia, M.R., et al., "The Generation of Molecular Diversity," *Bioorganic & Medicinal Chemistry Letters*, (1993), 3:387–396.

Prato, M., et al., "Addition of Azides to $C_{60}$: Synthesis of Azafulleroids," *J. Am. Chem. Soc.*, (1993), 115:1148–1150.

Prato, M., et al., "[3+2] Cycloadditions of $C_{60}$," *J. Am. Chem. Soc.*, (1993), 115:1594–1595.

Sandberg, W.S., et al., "Engineering multiple properties of a protein by combinatorial mutagenis," *Proc. Natl. Acad. Sci.*, (1993), 90:8367–8371.

Saunders, M., et al., "[3]He NMR: A Powerful New Tool for Following Fullerene Chemistry," *J. Am. Chem. Soc.*, (1994), 116:3621–3622.

Schinazi, R.F., et al., "Synthesis and Virucidal Activity of a Water–Soluble, Configurationally Stable, Derivatized $C_{60}$ Fullerene," *Antimicrobial Agents and Chemotherapy*, (1993), 37:1707–1710.

Seshadri, R., et al., "Addition of Amines and Halogens to Fullerenes $C_{60}$ and $C_{70}$," *Tetrahedron Letters*, (1992) 2069–2070.

Seshadri, R. et al., "Electron Donor–Acceptor Complexes of the Fullerenes $C_{60}$ and $C_{70}$ with Amines," *Chemistry Letters*, (1993), 217–220.

Sijbesma, R., et al., "Synthesis of a Fullerene Derivative for the Inhibition of HIV Enzymes," *J. Am. Chem. Soc.*, (1993), 115:6510–6512.

Takeshita, H., et al., "High–pressure Diels–Alder Reaction of [60] Fullerene with several Tropones. Characterization of the 1:1–Cycloadducts," *J. Chem. Soc. Perkin Trans.*, (1994), 1433–1437.

Taylor, R., et al., "Formation of $C_{60}Ph_{12}$ by Electrophilic Aromatic Substitution," *J. Chem. Soc., Commun.*, (1992), 667–.

Taylor, R., et al., "Nucleophilic Substitution of Fluorinated $C_{60}$," *J. Chem. Soc., Chem. Commun.*, (1992), 665–667.

Vasella, A., et al., "Fullerene Sugars: Preparation of Enantiomerically Pure, Spiro–Linked C–Glycosides of $C_{60}$," *Angew. Chem. Intl. Ed. Engl.*, (1992), 31:1388–1390.

Wilson, S.R., et al., "Applications of Electrospray Ionization Mass Spectrometry to Neutral Organic Molecules Including Fullerens," *J. Am. Soc. Mass Spectrum*, (1993), 4:596–603.

Wilson, et al., "Automated Solid–Phase Synthesis of Fullerene Derivatives," *Electrochemical Society Proceedings*, 95–10:22–30.

Wooley, K.L., et al., "Fullerene–Bound Dentrimers: Soluble, Isolated Carbon Clusters," *J. Am. Chem. Soc.*, (1993), 115:9836–9837.

Wu, S., et al., "Ene Reaction of Fullerene $C_{60}$ and 4–Allylanisole. Introduction of Alkene to Buckminsterfullerene," *Tetrahedron Letters*, (1994), 35:919–922.

FIG. 2
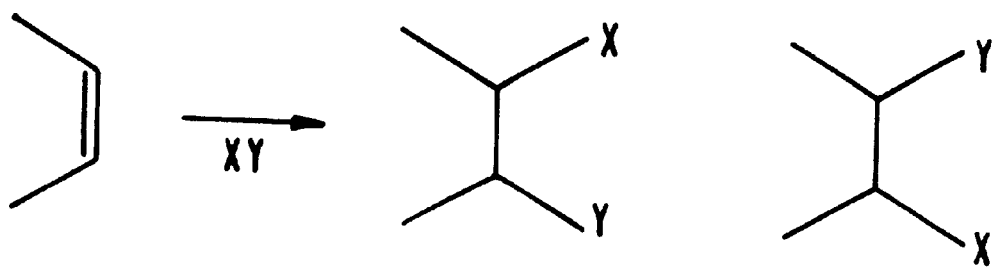
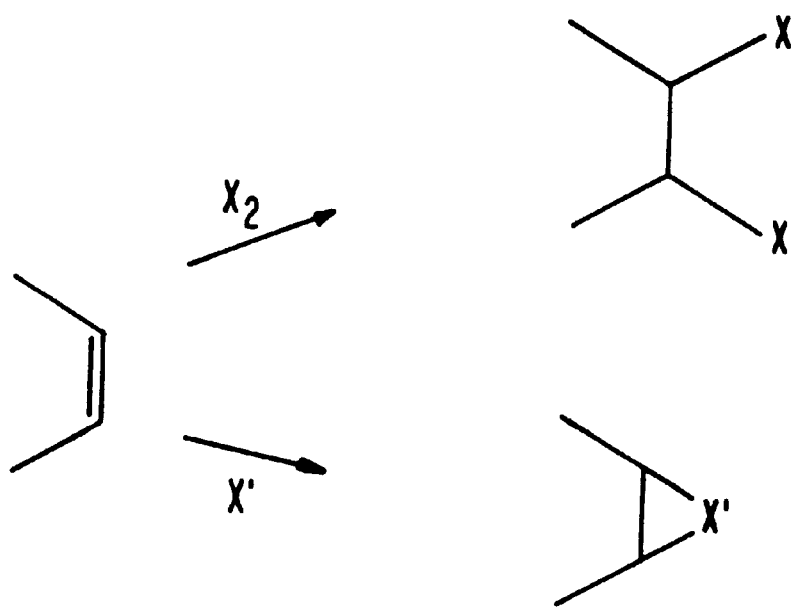
FIG. 3

MULTIPLY-SUBSTITUTED FULLERENES

CROSS-REFERENCE TO RELATED APPLICATIONS

This application is a continuation under 37 CFR §1.53(b) of application Ser. No. 08/969,261, filed Dec. 23, 1998, now 6,162,926, which is a file wrapper continuation application under former 37 CFR §1.62 of Ser. No. 08/509,209, filed Jul. 31, 1995, now abandoned.

FIELD OF THE INVENTION

The invention relates to methods of producing and characterizing compound libraries containing large numbers of multiply-substituted fullerenes. More particularly, the invention relates to chemically synthesizing combinatorial libraries of multiply-substituted fullerenes and to methods for efficiently screening for and identifying fullerene derivatives having pharmaceutical, materials science, or other utility. The invention also relates to the libraries thus produced, multiply-substituted fullerenes in the libraries which possess pharmaceutical, materials science, or other utility, and pharmaceutical formulations thereof.

BACKGROUND OF THE INVENTION

The traditional method of generating compounds with desirable biological activity involves identifying a lead compound with the desired biological activity; creating, one at a time, variants of that lead compound; and evaluating the biological activity of those variants. Usually, these new medicinal chemical lead structures originate from natural products isolated from microbiological fermentations, plant extracts, and animal sources; from pharmaceutical company compound databases containing a historic collection of compounds synthesized in the course of pharmaceutical research; and from the application of both mechanism-based and structure-based approaches to rational drug design.

Accordingly, the traditional method of finding active pharmacological compounds requires the synthesis of individual compounds and the evaluation of their biological activity. Many hundreds of compounds are typically synthesized and screened before a substance with significant activity is identified which can serve as the lead structure for the development of drug candidates. Once a lead compound is found, analogs are synthesized to optimize biological activity. In addition to being a costly method of determining lead compounds, the traditional method of drug discovery has the additional disadvantage that one can never synthesize all of the possible analogs of a given, promising lead compound.

Recent trends in the search for biologically active compounds have focused on the use of combinatorial chemistry for the preparation of potential sources of new leads for drug discovery. Combinatorial chemistry is a strategy which leads to large chemical libraries. It is often defined as the systematic and repetitive, covalent connection of a set of different "building blocks" of varying structures to each other to yield a large array of diverse, potentially pharmaceutically useful, molecular entities. Powerful techniques for the creation and screening of combinatorial libraries have been developed and improved upon rapidly in the past few years. These developments have rapidly expanded beyond their initial peptide and antibody targets to now include a wider range of biologically interesting compounds, as well as non-biological small molecules.

The libraries generated may each contain vast numbers of different molecules. Screening and isolation procedures are available which offer the means to identify and isolate compounds from a library which fulfill specific biological requirements. These methods include inhibition of binding of tritiated radioligands or selected fluorescence-labeled selected ligands to cell surface receptors on intact cells in culture, to cell surface receptors on disaggregated cell membranes, to cell surface receptors on cells in which a cloned neurotransmitter has been transfected, to cell surface receptors on tissue slices mounted upon microscope slides, to cell surface receptors on tissue strips maintained in organ baths, to cell surface receptors on whole organs maintained perfused and oxygenated in vitro, and to whole organs in the animal in vivo. The method also includes inhibition of binding of ligands to purified or cloned, recombinant receptors immobilized upon a chemical sensor, to purified or cloned, recombinant receptors immobilized upon an optical sensor, to purified or cloned, recombinant receptors immobilized upon an electromechanical sensor, and so forth. All of these techniques are well known to those skilled in the art.

The combinatorial chemistry approach does not actually change the medicinal chemistry paradigm. It introduces the new step of creating libraries, and accelerates the otherwise time consuming process of finding these compounds. By greatly increasing the range of molecular diversity available to the medicinal chemist, combinatorial chemistry has the potential to greatly broaden the number of molecules being surveyed for biological activity and other desirable properties.

The essential starting point for the generation of a diverse library of molecules is an assortment of small, reactive molecules which may be considered chemical building blocks. Unlike the traditional method, where the goal is to prepare and isolate individual variants of a lead compound, the combinatorial method deliberately creates a diverse set of variants simultaneously. The variants are then screened for useful properties.

Theoretically, the number of possible different individual compounds, N, prepared by an ideal combinatorial synthesis is determined by the number of blocks available for each step ("b") and the number of synthetic steps in the reaction scheme ("x"). If an equal number of building blocks are used in each reaction step, then $N=b^x$.

For example, it is well known in the art that multiple peptides and oligonucleotides may be simultaneously synthesized. In a single synthesis of a peptide, amino acids are simultaneously coupled to a chemically functionalized solid support. Typically, an N-protected form of the carboxyl terminal amino acid, e.g. a t-butoxycarbonyl protected (Boc-) amino acid, is reacted with the chloromethyl residue of a chloromethylated styrene divinylbenzene copolymer resin to produce a protected amino acyl derivative of the resin, the amino acid being coupled to the resin as a benzyl ester. This derivative is deprotected and reacted with a protected form of the next required amino acid thus producing a protected dipeptide attached to the resin. The amino acid will generally be used in activated form, e.g. a carbodiimide or active ester. The addition step is repeated and the peptide chain grows one residue at a time by condensation of the required N-protected amino acids at the amino terminus until the required peptide has been assembled on the resin. The peptide-resin is then treated with anhydrous hydrofluoric acid to cleave the ester linking the assembled peptide to the resin and liberate the required peptide. The protecting groups on side chain functional groups of amino acids which were blocked during the synthetic procedure, using conventional methods, may also be removed. This entire procedure may be automated. Multiple peptides or oligonucleotides may be synthesized.

One such methodology for peptide synthesis is disclosed in Geysen, et al. International Publication Number WO 90/09395, hereby incorporated by reference. Geysen's method involves functionalizing the termini of polymeric rods and sequentially immersing the termini in solutions of individual amino acids. Geysen's approach has proven to be impractical for commercial production of peptides since only very minute quantities of polypeptides may be generated. In addition, this method is extremely labor intensive.

U.S. Pat. No. 5,143,854 to Pirrung et al., hereby incorporated by reference, discloses another method of peptide or oligonucleotide synthesis. This method involves sequentially using light for illuminating a plurality of polymer sequences on a substrate and delivering reaction fluids to said substrate. A photochemical reaction takes place at the point where the light illuminates the substrates. Reaction at all other places on the substrate is prevented by masking them from the light. A wide range of photochemical reactions can be employed in this method, including addition, protection, deprotection, and so forth, as are well known in the art. This method of synthesis has numerous drawbacks, however, including the fact that the products are noncleavable and that the process produces large numbers, but only minute quantities, of products.

A further method and device for producing peptides or oligonucleotides is disclosed in European Patent No. 196174. The disclosed apparatus is a polypropylene mesh container, similar to a tea-bag, which encloses reactive particles. The containers, however, are not amenable to general organic synthesis techniques.

Further apparatus are disclosed in German Published Patent Application No. DE 4005518 and European Patent No. 0355582. This apparatus is not suitable for the synthesis of general organic compounds is directed to peptide or oligonucleotide synthesis.

The synthesis of general organic compounds poses many difficulties which are absent in the synthesis of peptides or oligonucleotides. For example, it is difficult to provide a device which will accommodate the wide range of synthetic manipulations required for organic synthesis. The synthesis of general organic compounds often requires such varied conditions as an inert atmosphere, heating, cooling, agitation, and an environment to facilitate reflux. Additionally, such synthesis requires chemical compatibility between the materials used in the apparatus for multiple synthesis and the reactants and solvents. Consequently, the apparatus must be constructed of materials which are resistant to organic synthesis conditions and techniques. organic synthesis also often requires agitation. Such agitation may be accomplished by magnetic stirring, sonicating or rotational shaking. None of the prior art devices are suitable for use under these special conditions required for general organic synthesis.

Techniques have been developed in which libraries of organic compounds are synthesized on a solid support and screened for promising lead compounds. For example, U.S. Pat. No. 5,288,514 to Ellman et al., hereby incorporated by reference, describes the combinatorial synthesis of benzodiazepine compounds on a solid support. Solid phase syntheses have been found to be suitable for automation, and these chemical and biological methods have recently been refined for the generation of large combinatorial libraries that are screened against a specific receptor or enzyme in order to determine the key molecular recognition elements of the compounds for that receptor or enzyme.

While combinatorial synthesis of linear peptides or oligonucleotides is easier than synthesis of non-peptide organic compounds, peptides in general are not promising therapeutic agents. Their limited utility as bioavailable therapeutic agents is due to problems related to drug delivery and metabolism that are well known to those skilled in the art. For example, peptide therapeutics generally can only be administered by injection or inhalation, rather than orally, which is preferred for medications which are to be administered regularly outside of a doctor's office. They also tend to have rapid clearing times. Furthermore, there remain major difficulties in targeting the peptide to the anatomical location where its action is desired.

For these reasons, there has been interest in the chemical synthesis of modified peptides, containing N-methylated backbones, peptide aldehydes, and peptide bonds replaced with methylene linkages, for example, which result in increased permeability through cell membranes and decreased metabolic destruction or destruction by enzymes. However, the synthesis of such modified peptides is expensive and complex, and the design of appropriate analogs to natural peptides frequently is far from straightforward. Further, the building blocks utilized are, in general, limited, even allowing for the use of unnatural enantiomers or artificial amino acids and modified nucleotides. The peptides or oligonucleotides generated possess a repetitive linkage through an amide or phosphate moiety, which limits their structural diversity.

The difficulties with peptides have created a need for small molecular templates suitable for substitution utilizing combinatorial methods to produce compounds with chemical, pharmaceutical and related utilities. Of particular value are templates capable of producing compounds useful as drugs for the targeting of enzymes, regulatory proteins and cellular receptors.

Agonists and antagonists of various receptors having central nervous system (CNS) activity are of great interest. For example, adenosine receptor agonists and antagonists have a wide range of potential therapeutic utilities. In the cardiovascular system, A-2 agonists can increase coronary blood flow and can serve as peripheral vasodilators. A-2 agonists have been shown to possess antipsychotic activity in the appropriate preclinical animal models and can also have desirable sedative properties. More speculatively, adenosine receptor agonists may also be effective as antihypertensive agents, in the treatment of opiate withdrawal, as modulators of immune competence and renin release, antiasthmatics, and in the treatment of respiratory disorders.

Calcium channels are physiologically very important because they have a central role in regulating intracellular $Ca^{2+}$ levels, which are vitally important for cell viability and function. $Ca^{2+}$ functions in many ways as a hormone and second messenger. $Ca^{2+}$ concentrations are implicated in the normal function of a number of vital processes, such as neurotransmitter release, muscle contraction, pacemaker activity, and secretion of hormones and other substances. A number of compounds useful in treating various diseases such as hypertension in animals, including humans, exert their beneficial effects by modulating functions of voltage-dependent calcium channels. It is well known that accumulation of calcium in the brain cells (calcium overload) is seen after periods of uncontrolled hyperactivity in the brain, such as after convulsions, migraine, anoxia and ischemia. As the concentration of calcium in the cells is of vital importance for the regulation of cell function, an uncontrolled high concentration of calcium will lead to the symptoms and possibly also the degenerative changes combined with the above diseases. Therefore, $Ca^{2+}$ blockers selective for brain cells will be useful in the treatment of anoxia, traumatic injury, ischemia, migraine and epilepsy.

L-glutamic acid, L-aspartic acid and several other closely related amino acids have in common the ability to activate neurons in the central nervous system. Acidic amino acids are well known to be neurotransmitters for the vast majority of excitatory neurons. However, the excessive or inappropriate stimulation of excitatory amino acid receptors can lead to neuronal cell damage via a mechanism known as excitotoxicity. This process has been suggested to mediate neuronal degeneration in a plethora of disease processes. Therefore, the amelioration of these degenerative neurological processes is an important therapeutic goal.

Excitatory amino acids exert their actions through specific receptors located postsynaptically or presynaptically. Such ion-channel-linked receptors are subdivided into three groups based on electrophysiological and neurochemical evidence: the NMDA (N-methyl-D-aspartate) receptors, the quisqualate receptors, and the kainate receptors. L-glutamic acid and L-aspartic acid probably activate all of the three types of excitatory amino acid receptors.

OBJECTS OF THE INVENTION

In view of the limitations and shortcomings of the prior art, it is apparent that there still remains a need to provide small molecular templates suitable for substitution utilizing combinatorial methods. It is therefore an object of this invention to provide novel organic compounds with pharmaceutical, materials science or other utility.

It is another object of this invention to provide a method for preparing libraries of said compounds or their pharmaceutically acceptable salts.

A further object of this invention is to provide methods for identifying and isolating the members of said libraries.

Yet another object of this invention is to provide a method for the screening of said libraries to determine the activity of the compounds therein and for the separation of the biologically active compounds in said libraries from the inactive compounds.

Still another object of this invention is to provide novel pharmaceutical and controlled-release compositions and methods for treatment utilizing said biologically active compounds.

Still another object of this invention is to provide methods for using the compounds of said libraries for diagnostic purposes and in biosensors.

Additional objects and advantages of the invention will be set forth in the description that follows.

SUMMARY OF THE INVENTION

The invention is directed to a method for the preparation and screening, preferably in parallel and simultaneous fashion, of large numbers of multiply-substituted fullerene derivatives. A method is provided for the preparation of combinatorial libraries of multiply-substituted fullerene compounds, some of which compounds possess pharmaceutical, materials science, or other utilities.

The invention also relates to novel multiply-substituted fullerenes which possess useful biological activity and to pharmaceutical formulations thereof, as well as precursors for making them. These multiply-substituted fullerenes have the general structure of formula I:

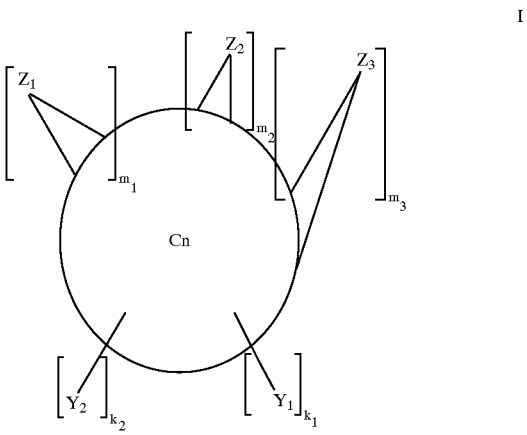

wherein:

$Z_1$, $Z_2$ and $Z_3$ are absent or present, provided that at least one is present, and are independently selected from the group consisting of —$CR_1R_2$—, —$CR_1R_2$—$CR_3R_4$—, —$NR_1$—, —O—$CR_1R_2$—, —S—$CR_1R_2$—, —$NR_1$—$CR_2R_3$—, —$R_1R_2C$—$NR_3$—$CR_4R_5$—, —$R_1C$=N—$CR_2R_3$—, —$R_1R_2C$—$NR_3$—$NR_4$—, —$R_1R_2C$—$NR_3$—O—, —N=$NR_1$—, —N=N—$NR_1$—, —N=N—$CR_1R_2$—, —O—$NR_1$—O—, —$R_1R_2C$—O—$CR_3R_4$—, —$R_1R_2C$—O—$NR_3$—, —$R_1C$=N—$NR_2$—, —$R_1C$=N—O—, —$R_1N$—$NR_2$—$NR_3$—, —$R_1N$—$NR_2$—O—, —$CR_1R_2$—$CR_3R_4$—$CR_5R_6$—, —$CR_1R_2$—$CR_3$=$CR_4$—, —$CR_1R_2$—$CR_3R_4$—$CR_5CR_6$—$CR_7R_8$—, —$CR_1$=$R_2$—$CR_3R_4$—$CR_5R_6$—, —$CR_1R_2$—$CR_3$=$CR_4$—$CR_5R_6$—, —$CR_1$=$CR_2$—$CR_3$=$CR_4$— and —$CR_1R_2$—$CR_3$=C=$CR_4$— such that $Z_1$, $Z_2$ and $Z_3$ are each attached to the carbon skeleton of the fullerene structure by two single bonds selected from the group consisting of C—C, C—O, C—S or C—N, the unsatisfied valences of each Z moiety being the location of those bonds;

$R_1$, $R_2$, $R_3$, $R_4$, $R_5$, $R_6$, $R_7$ and $R_8$ may be the same or different and are selected from the group consisting of hydrogen, oxygen, lower alkyl, higher alkyl, cycloalkyl, alkenyl, alkynyl, alkoxy, carboxylic acids, carboxylic esters, alkylthio, thioalkyl, aryl, aryloxy, aralkyl, primary amine, secondary amine, amino acid side chains, and heterocycles, such that C together with any two R groups bonded thereto may form an oxo or thioxo group, hydrocarbon ring or heterocycle;

$Y_1$ and $Y_2$ are absent or present, provided that at least one is present, and are selected from the group consisting of hydrogen, lower alkyl, higher alkyl, cycloalkyl, alkenyl, alkynyl, alkoxy, alkylthio, thioalkyl, aryl, aryloxy, aralkyl, primary amine, secondary amine, amino acid side chains,. and heterocycles;

$20 < n < 240$;

$(k_1 + k_2)$ is 1 to n; and $(m_1 + m_2 + m_3)$ is 1 to n/2, with the limitation that $2(m_1 + m_2 + m_3) + (k_1 + k_2) \leq n$;

or a salt or addition compound thereof;

or the general structure of formula II:

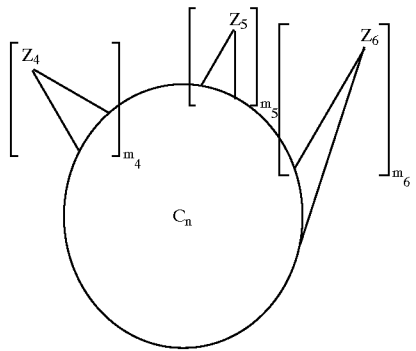

II wherein:

$Z_4$, $Z_5$ and $Z_6$ are absent or present, provided that at least two are present, and are independently selected from the group consisting of —CR$_9$R$_{10}$—, —CR$_9$R$_{10}$—CR$_{11}$R$_{12}$—, —NR$_9$—, —O—CR$_9$R$_{10}$—, —S—CR$_9$R$_{10}$—, —NR$_9$—CR$_{10}$R$_{11}$—, —R$_9$R$_{10}$C—NR$_{11}$—CR$_{12}$R$_{13}$—, —R$_9$C=N—CR$_{10}$R$_{11}$—, —R$_9$R$_{10}$C—NR$_{11}$—NR$_{12}$—, —R$_9$R$_{10}$C—NR$_{11}$—O—, —N=NR$_9$—, —N=N—NR$_9$—, —N=N—CR$_9$R$_{10}$—, —O—NR$_9$—O—, —R$_9$R$_{10}$C—O—CR$_{11}$R$_{12}$—, —R$_9$R$_{10}$C—O—NR$_{11}$—, —R$_9$C=N—NR$_{10}$—, —R$_9$C=N—O—, —R$_9$N—NR$_{10}$—NR$_{11}$—, —R$_9$N—NR$_{10}$—O—, —CR$_9$R$_{10}$—CR$_{11}$R$_{12}$—CR$_{13}$R$_{14}$—, —CR$_9$R$_{10}$—CR$_{11}$=CR$_{12}$—, —CR$_9$R$_{10}$—CR$_{11}$R$_{12}$—CR$_{13}$CR$_{14}$—CR$_{15}$R$_{16}$—, —CR$_9$=R$_{10}$—CR$_{11}$R$_{12}$—CR$_{13}$R$_{14}$—, —CR$_9$R$_{10}$—CR$_{11}$=CR$_{12}$—CR$_{13}$R$_{14}$—, —CR$_9$=CR$_{10}$—CR$_{11}$=CR$_{12}$— and —CR$_9$R$_{10}$—CR$_{11}$=C=CR$_{12}$—, such that $Z_4$, $Z_5$ and $Z_6$ are each attached to the carbon skeleton of the fullerene structure by two single bonds selected from the group consisting of C—C, C—O, C—S or C—N, the unsatisfied valences of each Z moiety being the location of those bonds;

$R_9$, $R_{10}$, $R_{11}$, $R_{12}$, $R_{13}$, $R_{14}$, $R_{15}$ and $R_{16}$ may be the same or different and are selected from the group consisting of hydrogen, oxygen, lower alkyl, higher alkyl, cycloalkyl, alkenyl, alkynyl, alkoxy, carboxylic acids, carboxylic esters, alkylthio, thioalkyl, aryl, aryloxy, aralkyl, primary amine, secondary amine, amino acid side chains, and heterocycles, such that C together with any two R groups bonded thereto may form an oxo or thioxo group, hydrocarbon ring or heterocycle;

$20 < n < 240$; and $(m_4 + m_5 + m_6)$ is 2 to n/2;

or a salt or addition compound thereof;

or the general structure of formula III:

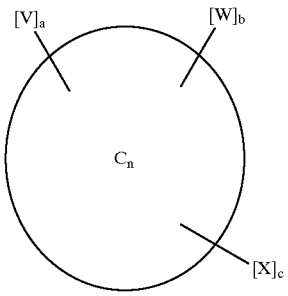

III wherein:

V, W and X are absent or present, provided that at least two are present, and are selected from the group consisting of hydrogen, lower alkyl, higher alkyl, cycloalkyl, alkenyl, alkynyl, carboxylic acids, carboxylic esters, alkoxy, alkylthio, thioalkyl, aryl, aryloxy, aralkyl, primary amine, secondary amine, amino acid side chains, and heterocycles;

$20 < n < 240$; and $(a+b+c)$ is 1 to n/2;

or a salt or addition compound thereof. Preferably n is 60, 70 or a mixture of 60 and 70.

Preferred specific compounds include those compounds wherein the substituents contain functional groups which are amino acid side chains, or analogs of amino acid side chains.

The preparation of libraries of multiply-substituted fullerene libraries may result in the preparation of compounds which possess pharmaceutical, materials science, or other utility. Certain of the fullerene derivatives may be useful as drugs for the targeting of enzymes, regulatory proteins and receptors of various kinds. In particular, certain multiply-substituted fullerenes of the claimed invention may be used in pharmaceutical compositions for the treatment of various central nervous system, cardiovascular and respiratory disorders. Multiply-substituted fullerenes may also be used to form compositions for the controlled release of fragrances, pigments, moisturizers and other small molecules.

Other fullerene derivatives may be useful for, e.g., (i) the construction of batteries and similar devices such as fuel cells with improved electrochemical properties yielding typically increased storage times and at elevated currents; (ii) the construction of semiconductor devices such as diodes, transistors, field-effect devices, Josephson devices, superconducting quantum interference devices, electro-optically emissive diodes, transistors, and current-injection devices, and the like; (iii) the construction of electroluminescent display devices such as flat-screen displays; (iv) the construction of electrical, optical, mechanical, magnetic, curie-point, or similar memory-storage devices such as are used in digital computers for the storage of binary information, including holographic or other optical-transform memory storage techniques; (v) the formulation, compounding, production, machining, and packaging of materials with superconductive properties; (vi) the formulation, compounding, production, machining, and packaging of materials with useful mechanical properties, typified by shear strength, Young's modulus, ductility or other Theological characteristics, bulk modulus, lowered coefficient of friction in contact with any other material, and so forth; (vii) the formulation, compounding, production, machining, and packaging of materials with useful thermal properties, such as high thermal conductivity; (viii) the formulation, compounding, production, and packaging of materials with useful magnetic properties such as paramagnetism, diamagnetism, high or low magnetic susceptibility, unusual Curie point or Neel temperature, and the like. Materials science properties of fullerenes and fullerene deviations are based on unusual redox properties and the ability of metal salts to display conductivity and superconductivity.

In another embodiment, a method is provided for screening the libraries for active compounds which comprises the steps of (a) contacting multiply-substituted fullerene compounds from the library with a biological target of interest, and (b) separating compounds which interact with the biological target from the inactive compounds. In this embodiment, compound libraries are screened for biological activity by means of receptor binding assays or in vitro physiometric assays. In the most preferred embodiment, solid phase receptor binding assays are performed using a cloned receptor.

In a further embodiment, a method is provided for the separation of the active compounds from the inactive compounds. According to this method, libraries of multiply-substituted fullerenes can be indexed spectroscopically so that a desired compound can be identified and isolated from the library.

The invention also relates to the use of labelled fullerenes with the ability to target tumor cells as diagnostic agents, as well as the use of multiply-substituted fullerenes having biological activity in biosensors to detect analytes of interest.

The invention further relates to the preparation of monolayers and bilayers comprising multiply-substituted fullerenes in combination with a lipid.

BRIEF DESCRIPTION OF THE DRAWINGS

FIG. 2 is a schematic illustration of the addition of XY to a 6/6 bond of $C_{60}$.

FIG. 3 is a schematic illustration of the addition of $X_2$ or a symmetric group $X^1$ to a 6/6 bond of $C_{60}$.

DETAILED DESCRIPTION OF THE INVENTION

Figure 1:
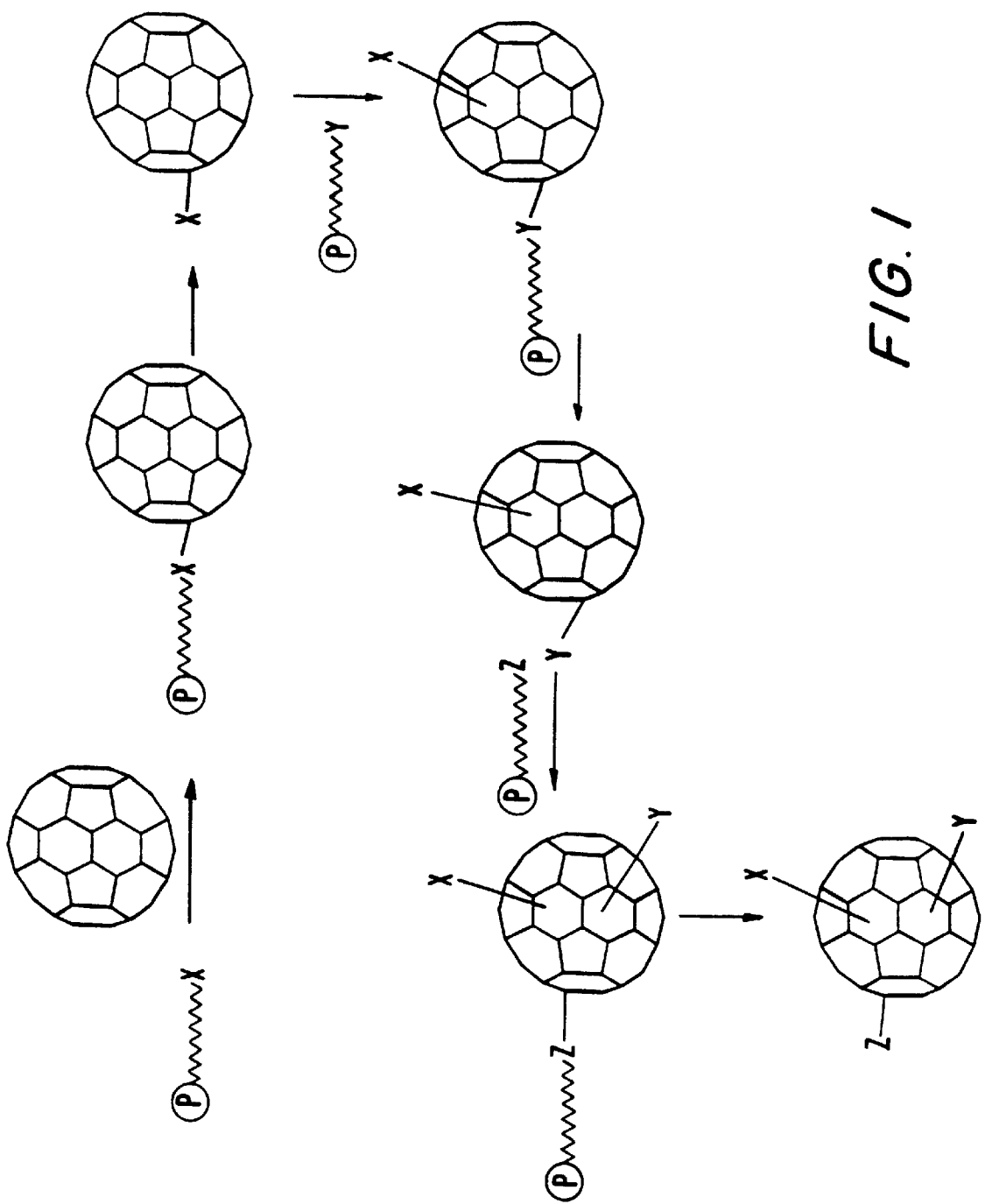
FIG. 1 is a schematic illustration of bead-based synthesis of multiply-substituted fullerenes.

Fullerenes are cage-like molecules composed entirely of carbon atoms in the $sp^2$-hybridized state, and constitute the third form of pure carbon. The other two pure forms are diamond and graphite. Typically, fullerenes each have 12 pentagons, but differing numbers of hexagons. The most abundant species is the $C_{60}$ molecule or Buckninsterfullerene, one of the first fullerenes to be produced in gram quantities. $C_{60}$ is a truncated icosahedron, the highest symmetry structure possible, having 12 pentagons and 20 hexagons. The second most abundant species of the fullerene family is $C_{70}$. To date, fullerenes containing up to 400 carbon atoms have been identified; for example $C_{24}$, $C_{30}$, $C_{60}$, $C_{70}$, $C_{76}$, $C_{78}$, $C_{84}$, $C_{90}$, $C_{94}$, $C_{96}$, and $C_{120}$ have been isolated.

Fullerenes, particularly $C_{60}$, are known in the art to be useful materials for the construction of electronic devices, chemical catalysts, chromatographic separation media, durable coatings, and similar applications which take advantage of the unique properties of this allotrope of carbon.

Fullerenes are produced by high temperature vaporization of solid graphite rods by resistive heating or arc heating in the presence of a few to several torr of rare gas. The soot produced by the vaporization contains varying levels of fullerenes, depending on the vaporization conditions.

The molecular structure for buckminsterfullerene was first identified in 1985 by Kroto et al. and reported in *Nature*, 318:162–163 (1985). The process described therein for making fullerenes involves vaporizing the carbon from a rotating solid disk of graphite into a high-density helium flow using a focused pulsed laser. That process did not utilize a temperature controlled zone for the growth and annealing of fullerene molecules from the carbon vapor formed by the laser blast. Only microscopic quantities of fullerenes were produced by this process.

International Patent Application No. WO92/04279 published on Mar. 19, 1992, discloses a method for producing fullerenes involving the resistive or arc heating of graphite in the presence of an inert quenching gas to form a black soot material which contains fullerenes. $C_{60}$ is the predominant fullerene produced by the process.

U.S. Pat. No. 5,316,636 to Bunshah et al., discloses a process for producing fullerenes by electron beam evaporation of a carbon target in a vacuum. The evaporated carbon atoms or clusters are deposited onto collection substrates which are electrically charged and heated, or neutral and chilled. The resulting carbon soot is extracted to recover fullerenes. This process produces carbon soot which is rich in $C_{70}$ and higher fullerenes.

Still another method of making fullerenes is described in U.S. Pat. No. 5,300,203, which discloses that fullerenes can be efficiently generated by vaporizing carbon with a laser beam and maintaining the vaporized carbon at conditions selected to promote fullerene growth and formation. This method of fullerene generation may be used to form new compounds including fullerenes surrounding one or more metal atoms, and fullerenes wherein one or more carbon atoms have been substituted with boron or nitrogen.

Thus, it is clear that there are a multiplicity of methods for the preparation of $C_{60}$ itself as well as its higher homologues such as $C_{70}$, $C_{84}$, and so forth, such that one ordinarily skilled in the art can obtain such materials. Indeed, the recent employment of these technologies has allowed $C_{60}$ to be produced on a multi-ton scale annually (MER Corporation, Tucson, Ariz.).

It is contemplated that carbon nanotubes, as first prepared by Iijima [S. Iijima, *Nature*, 354:56–58 (1991)], may also be used with the procedures described in this invention. This is based on the structural similarity of the endcaps of these tubes to fullerenes and the curved nature of the tubule surfaces which is characteristic of fullerenes such as $C_{60}$ and $C_{70}$. While nanotubes for the most part do not closely resemble fullerenes chemically, the ends and junctional regions, comprising approximately one to two percent of the structure, do react chemically in the manner of pure fullerenes.

Substituted Fullerenes

Methods have been developed to substitute fullerenes with a variety of substituents. Of particular interest are fullerene substitutions utilizing Diels-Alder reactions. Multiple Diels-Alder reactions provide means for attaching of substituents to the fullerene by means of multiple single bonds. Other methods used to substitute fullerenes include:

(1) 1,3-Dipolar Additions

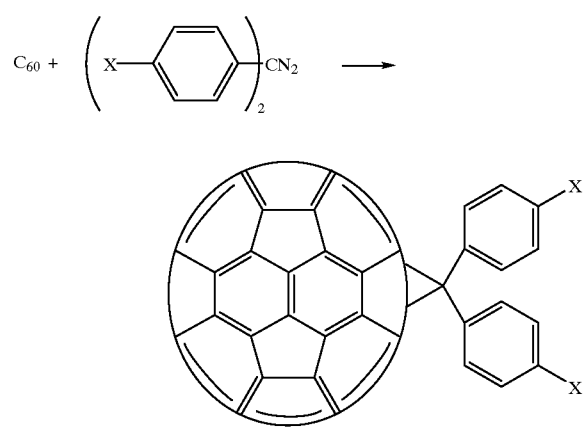

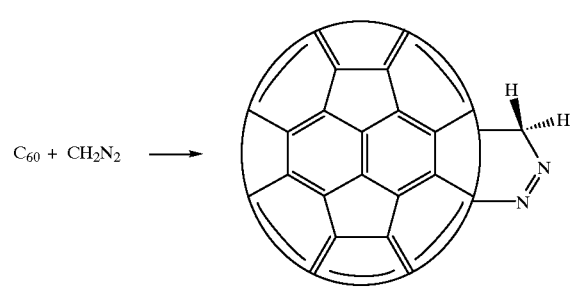

Sijbesma et al., *J. Am. Chem. Soc*, (1993), 115:6510–12;

Suzuki T., *J. Am. Chem. Soc.* (1992) 114:7301–02;

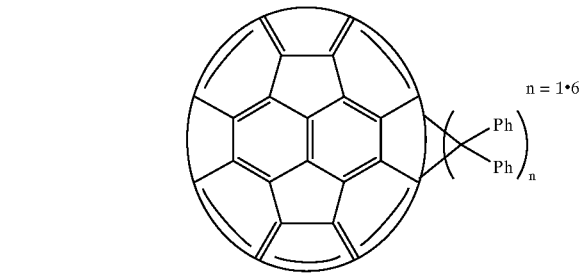

Suzuki et al., *Science* (1991) 254:1186–88;

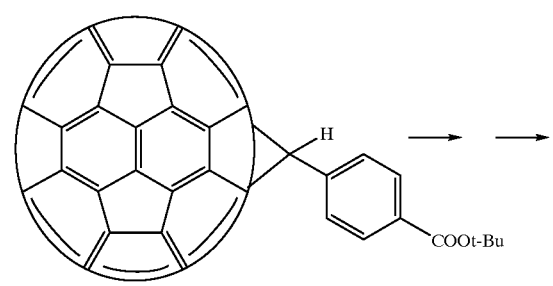

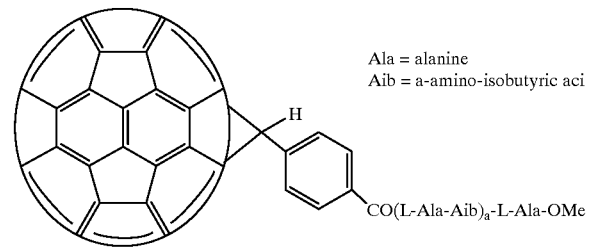

Prato et al., *J. Org. Chem.* (1993) 58:5578–5580;

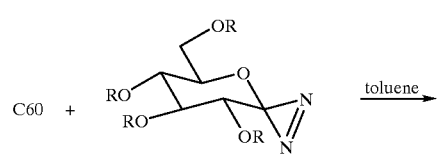

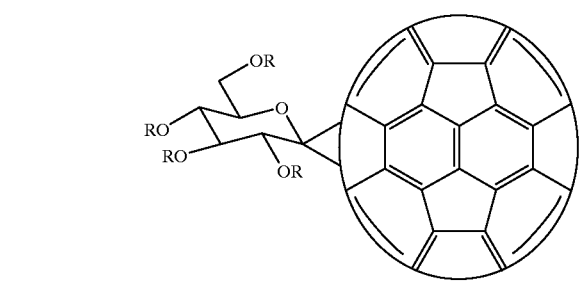

R = Bn.Piv (Pivaloyl)

Vasella A. et al., *Angew. Chem. Int. Ed. Engl.* (1992) 31:1388–1390;

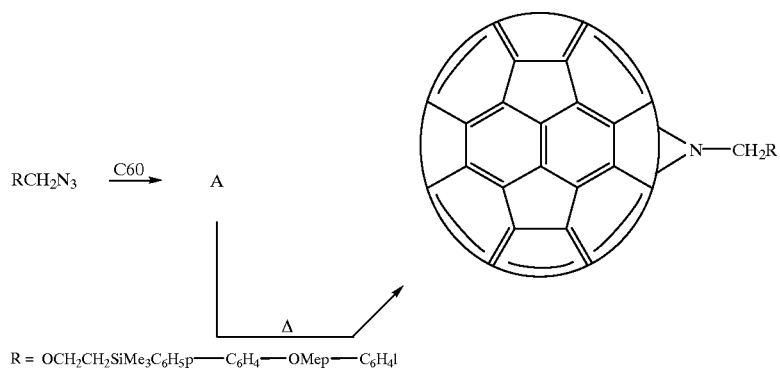
Prato M. et al., *J. Am. Chem. Soc.* (1993) 115:1148–50;
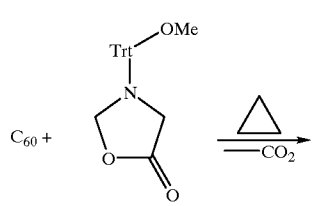
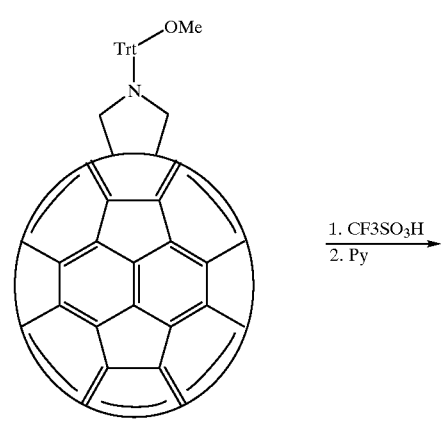
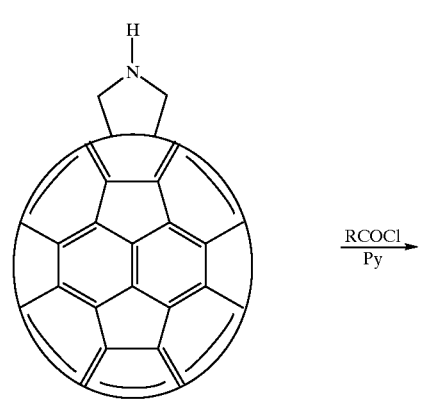
Maggini, M. et al., *Tetrahedron Lett.* (1994) 35:2985–88;
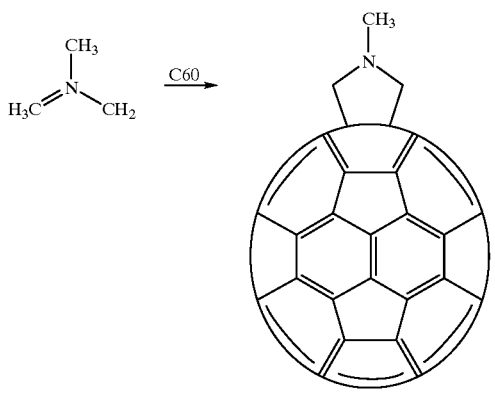

-continued
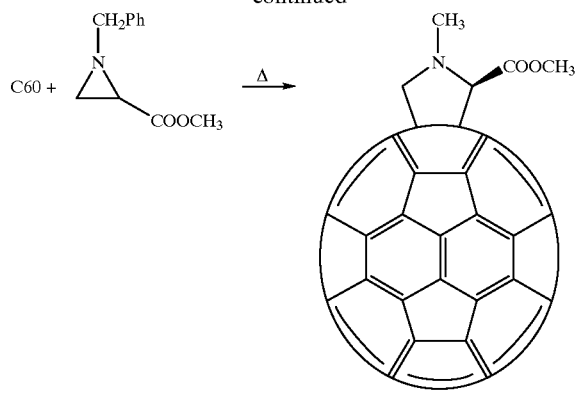
Maggini, M. et al., *J. Am. Chem. Soc.* (1993) 115: 9798–99];
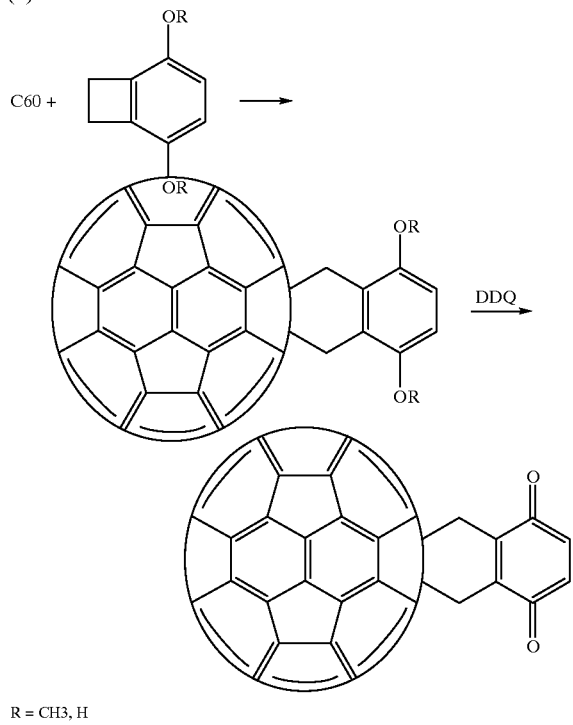
R = CH₃, p-C₆H₄OMe
Meier, M. S. et al., *J. Am. Chem. Soc.* (1994) 116: 7044–7048;
(2) Diels-Alder Reactions
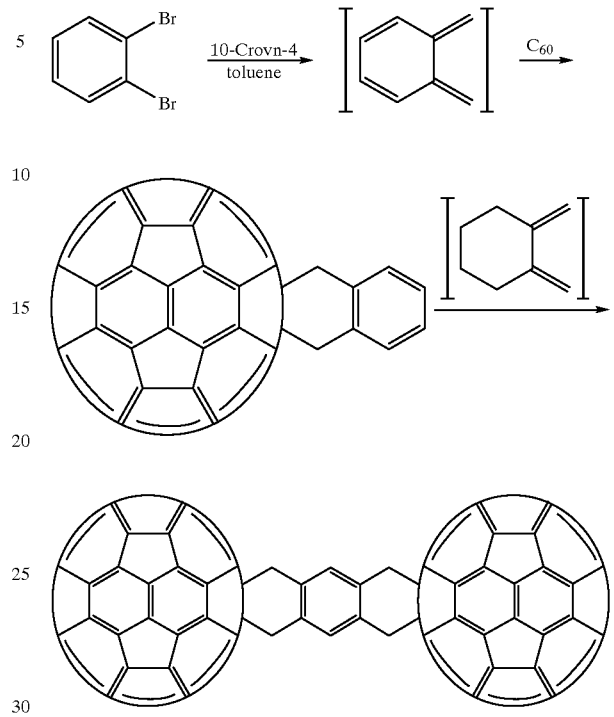
R = CH3, H
Iyoda et al., *J. Chem. Soc. Chem. Commun.* (1994) 1929–1930;
Belik, P. et al., *Angew. Chem. Int. Ed. Engl.* (1993) 32: 78–80;
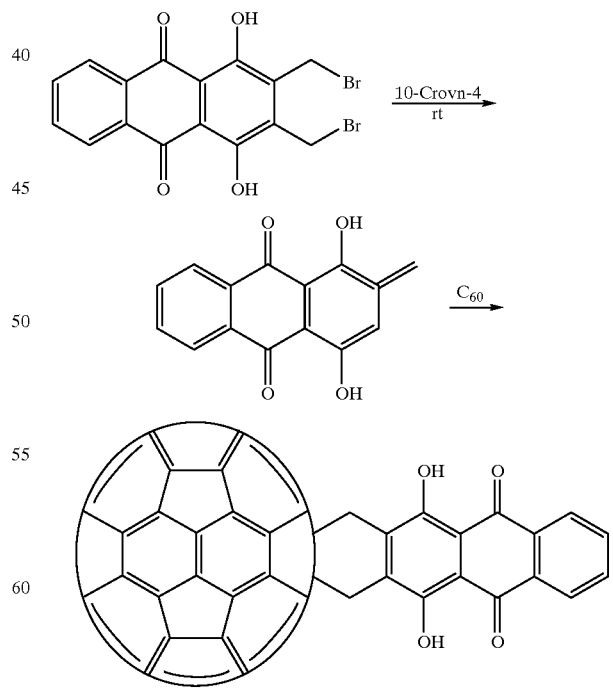

-continued
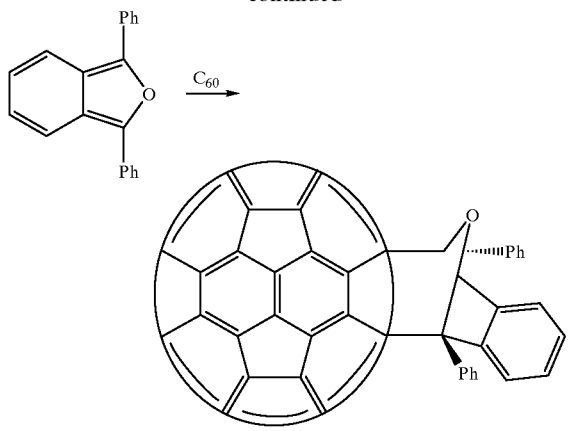
Bidell, W. et al., *J. Chem. Soc. Chem. Commun.* (1994) 1641–164;
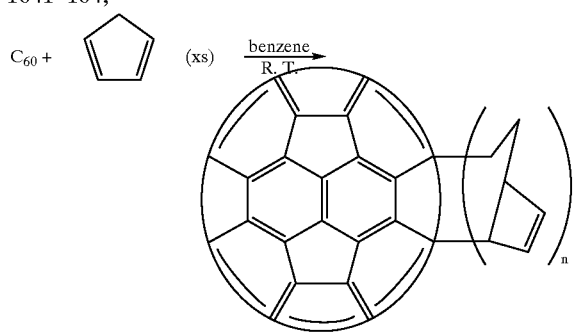
Meidine, M. F. et al., *J. Chem. Soc. Chem. Commun.* (1993), 1342–1344;
(3) Other Cycloaddition Process
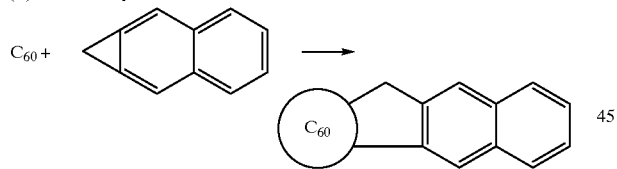
Saunders, M. et al. *Tetra. Lett.* (1994) 35:3869–3872;
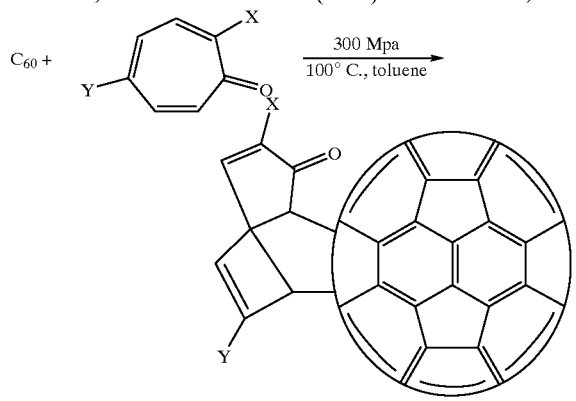
Tadeshita, H. et al. *J. Chem. Soc. Perkin Trans.* (1994) 1433–37
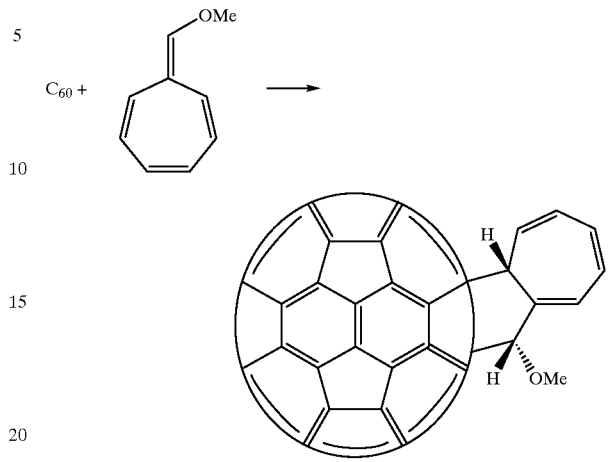
Beer, E. et al. *Angew. Chem. Int. Ed. Engl.* (1994) 33:1087–1088;
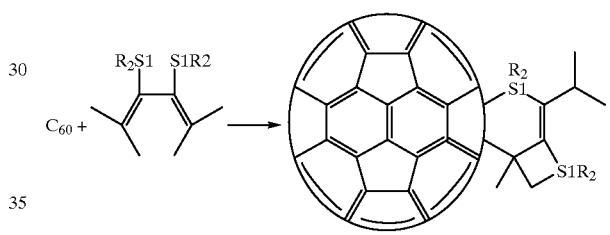
$R = {}_nPr, Et$
Kusukawa, T. et al. *Organomettallics* (1994) 13:4186–4188;
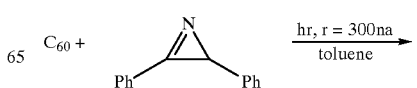

Wilson, S. R. *J. Org. Chem.* (1993) 58:6548–6549;
4. Cyclopropanation by Addition/Elimination
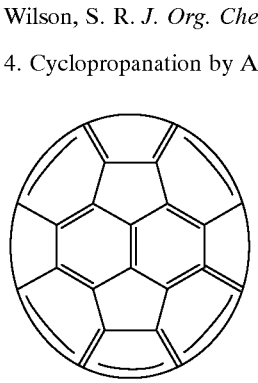
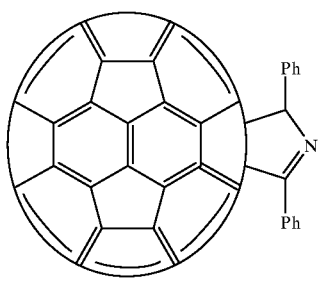
Averdung, J. et al. *Chem. Ber.* (1994) 127:787–789;
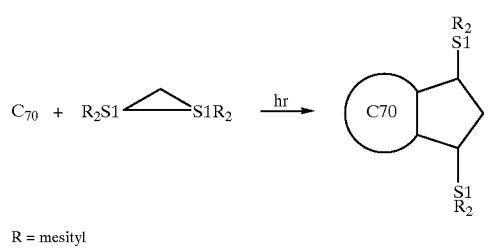
R = mesityl
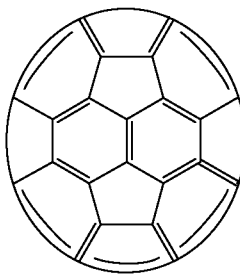
Akasaka, T. et al. *J. Am. Chem. Soc.* (1994) 116:2627–28;
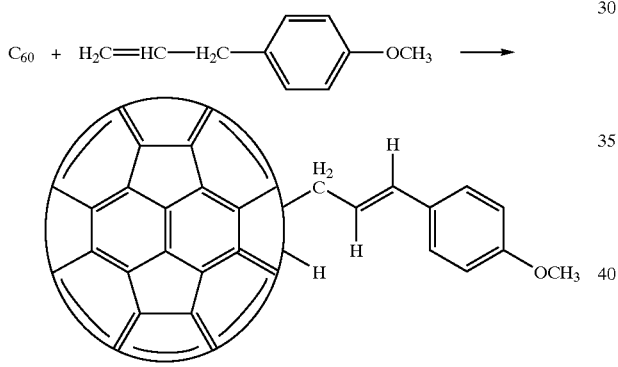
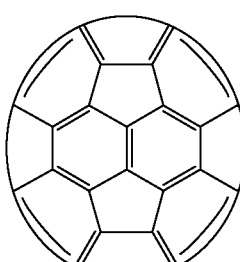
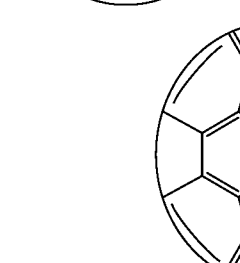
Wu, S. H. et al., *Tetra. Lett.* (1994) 35:919–22;
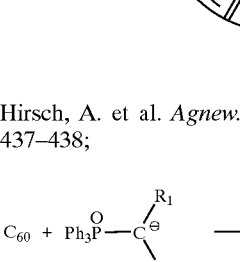
Hirsch, A. et al. *Agnew. Chem. Int. Ed. Engl.* (1994) 33: 437–438;
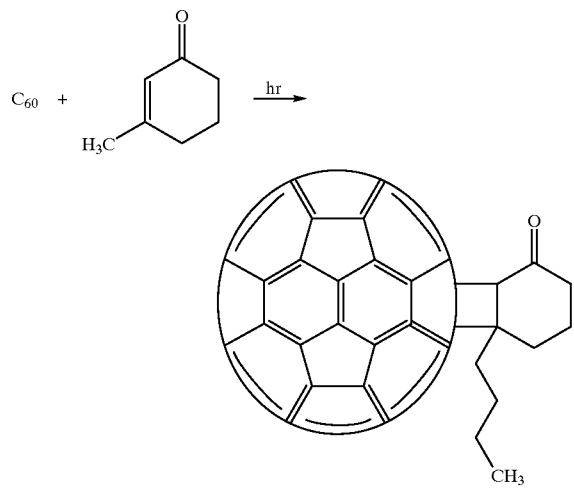
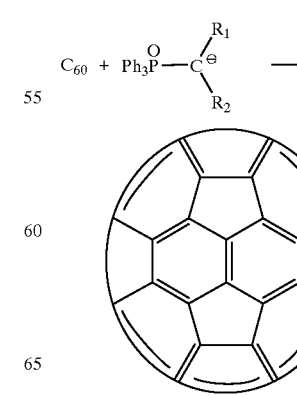

21
-continued

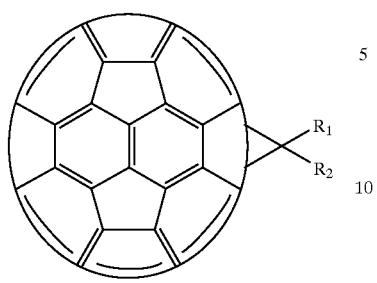

R₂ = H₂ R₁ = CH₃ C₁₁H₂₃ (CH₂)₈—CH=CH₂ (CH₂)₂COOC₂H C₆H₅ 5-C₆H₅

Bestmann, H. J. et al. *C. Tetra. Lett.* (1994) 35:9017–9020;

5. Addition of Carbanions/Alkyl lithiums/Grignards

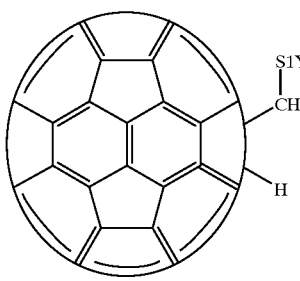

Y = Me, H, Ph.

Nagashima, H. et al. *J. Org. Chem.* (1994) 59:1246–1248;

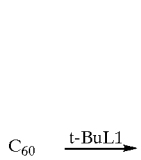

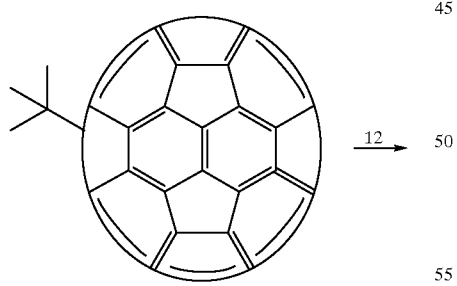

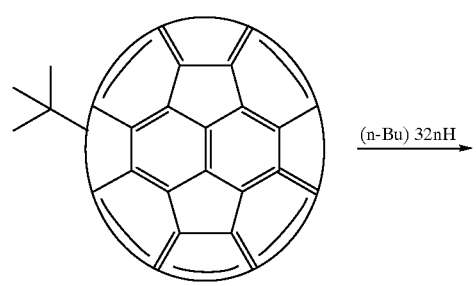

22
-continued

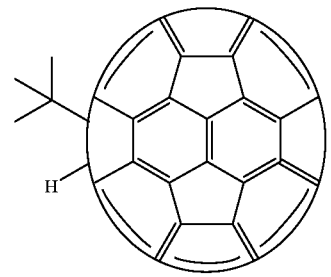

Fagan, P. G. et al. *J. Am. Chem.* (1994) 114:9697–99;

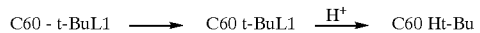

Hirsch, A. et al. *Agnew. Chem. Int. Ed. Engl.* (1992) 31:766–78;

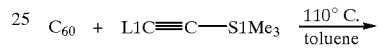

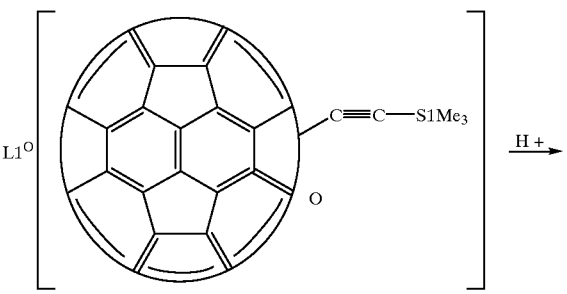

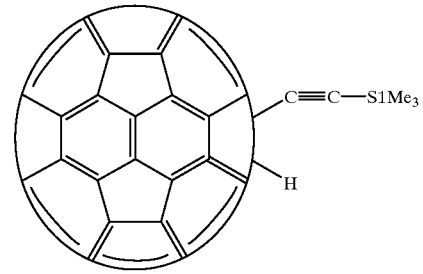

45%

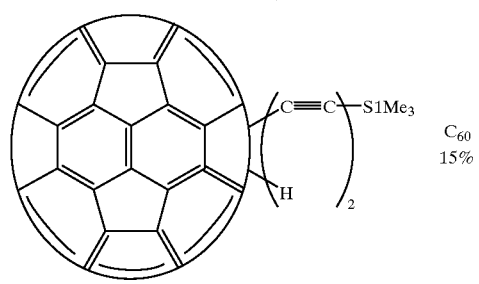

16%

Komatsu, K. et al., *J. Org. Chem.* (1994) 59:6101–02.

The reaction of diazo compounds in a three-step sequence starting from the N-aryl glycine to provide R-substituted fullerenes wherein R is aryl, alkyl, or aralkyl is taught by Prato et al. in *J. Org. Chem.* 58(21):5578–5580 (1993).

Multiple products are obtained when the reaction is allowed to run for a period of time beyond that required for monosubstitution. However, all groups were the same and no attempt was made to characterize these multiple products either with regard to their degree of substitution or the geometrical nature of the substitutions.

Multiply-substituted fullerenes wherein all groups are the same are known as well. However, combinatorial methods of synthesis until now have not been used for the synthesis of libraries of multiply-substituted fullerenes, and characterization of particular geometric isomers of multiply-substituted fullerenes generally has not been possible. Hawkins reported separation of the isomers of a multiply-substituted fullerene in which the substituent was a bidentate osmium cluster in *J. Am. Chem. Soc.* 114(20):7954–7955 (1992).

U.S. Pat. No. 5,294,732 to Chiang et al., hereby incorporated by reference, teaches polysubstituted fullerene moieties having a plurality of substituents selected from the group consisting of hydroxyl, oxide, nitro, amino, organocarboxy and amide. The polysubstituted fullerenes are disclosed as being useful as cross-linking agents in polymers and/or as core building blocks of star polymers. The patent discloses the use of either nitronium ion or an organic peracid to produce multiple electrophilic substitutions on a fullerene molecule, followed by a sequence of chemical transformation to introduce hydroxy, nitro, organocarboxy, amide, oxide, and amino groups onto the fullerene. However, the Chiang patent does not disclose the separation or identification of individual geometric isomers of the polysubstituted fullerene. The Chiang patent also teaches the transformation of multiply-substituted fullerenes containing nitro or hydroxyl groups to other useful chemical substituents and the use of mass spectral analysis which shows that the mixtures contain anywhere from ten to more than thirty-five individual components, but no scheme or process is disclosed to effect separation of these multiply-substituted compounds, nor to identify or otherwise differentiate them.

Because a fullerene of the formula $C_n$ has n sites for substitution, fullerenes are excellent candidates for combinatorial synthesis. Rather than increase the library by a power of N, as with traditional methods of combinatorial chemistry, the library is increased by a factor of nN. Thus, more compounds are synthesized in few steps.

Exohedral modification of fullerenes in three dimensions by addition reactions provides a profusion of reaction products and possible isomers. The fullerene core molecule provides for a multitude of locations to which individual moieties can be attached. Each moiety contains a functional group able to form a covalent bond with at least one carbon atom in the fullerene molecule. By attaching moieties on the fullerene in a distributed manner, many different fullerene derivatives can by synthesized. In essence, "designed diversity" is achieved.

Solid Phase Combinatorial Synthesis of Fullerenes

In an alternative embodiment of the invention a similar series of chemical coupling/cyclization steps are conducted, except that the synthesis steps are conducted on discrete solid supports such as beads. A general approach for bead-based synthesis in conjunction with peptides is described in Lam et al., *Nature* (1991) 354:82–84, and further described in PCT Application No. 92/00091 and Houghten et al., *Nature* (1991) 354:84–86, all of which are incorporated herein by reference.

FIG. 1 illustrates the synthesis of multiply-substituted fullerenes on such beads. A large number of beads are suspended in a suitable carrier in a container. Although only a single bead is illustrated in FIG. 1 for the purposes of simplifying the illustration, it will be recognized that a large number of beads are utilized. The beads are attached to an active reagent X, Y or Z via an optional linker molecule. It should be noted that while each reagent X, Y and Z in FIG. 1 is attached to a bead, it is not necessary that all be attached.

The reagent X, Y or Z can be the active precursor from any of the reactions discussed supra. For example, benzhydralamine resin (BHA) is N-linked with glycine to provide a N-BHA-glycine resin. N-BHA-glycine is heated with almost any aldehyde X and a fullerene to give resin-linked derivative as shown:

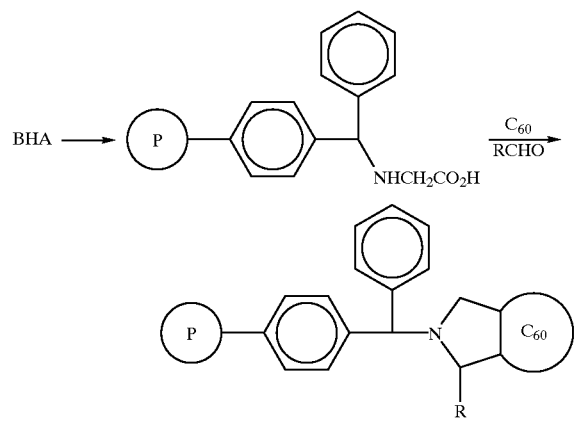

Cleavage of the product from the resin (usually with acid), leads to formation of substituted fullerene of the formula:

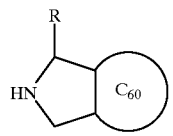

The entire process can be repeated. The process can be carried out using commercially available robotic synthesizers. In addition, the process could be carried out in a specially designed instrument wherein each activated resin (or in some cases its precursor) is contained in a sealed cartridge, which cartridges are then loaded into an apparatus to carry out each step of the synthesis in an automatic flow system. Flowing suitable fullerenes and reagents through the machine leads to production of $C_{60}$-XYZ compounds in an unattended manner.

In an additional modification of the synthesis, the beads are divided for coupling. The protecting groups are removed and reagents are added to the various containers.

Thereafter, the various beads are appropriately washed of excess reagents, and remixed. Again, it will be recognized that by virtue of the large number of beads utilized at the outset, there will similarly be a large number of beads randomly dispersed in the container, each having a particular first portion of the fullerene to be synthesized on a surface thereof.

The various beads are again divided for coupling and the beads are deprotected and exposed to a second, different portion of the reagent. Each bead eventually will have only a single type of molecule on its surface. In this particular embodiment, all of the possible molecules formed are present and attached to separate beads.

The beads are then exposed to a receptor of interest. In a preferred embodiment the receptor is fluorescently or radioactively labelled. Thereafter, one or more beads are identified that exhibit significant levels of the label using one of a variety of techniques. For example, in one embodiment, mechanical separation under a microscope is utilized. The identity of the molecule on the surface of such separated beads is then identified using, for example, NMR, electrospray mass spectrometry, electron impact mass spectrometry, conventional biochemical purification followed by capillary electrophoresis or denaturing gel electrophoresis followed by enzymatic cleavage and sequencing, or the like.

In alternative embodiments the identity of the molecule that is complementary to the receptor is determined with respect to the "bin" or container in which the labelled receptor is located. For example, by exposing the molecules in containers to the labelled receptor, the identity of one terminal portion of the molecule may be identified. For example, if fluorescence is noted after exposure to the molecules in container A, but not B or C, it is readily determined that the terminal molecule that produces a complementary receptor is "D."

Another aspect of the present invention is the use of fullerene libraries as cores on which to build peptide or other libraries. This modification is an important functional adaptation. For example, 29 different bis-substituted fullerenes are used to construct libraries in three dimensions with peptides, as shown in FIG. 1, wherein X, Y and Z=any amino acid residues. This non-linear growth of peptide libraries is unique and can be used with all other existing library methods.

Biological Activity of Substituted Fullerenes

Sijbesma et al. have disclosed the preparation of a simple monosubstituted fullerene derivative and its employment as an antagonist of the biological activity of the enzyme HIV protease in *J. Am. Chem. Soc.* 115(15):6510–6512 (1993). The fullerene derivative was developed using a traditional structure-based approach to its design, rather than a combinatorial chemistry approach.

Similarly, Schinazi and his colleagues have reported various enzyme inhibition activities of simple monosubstituted fullerene derivatives in *Antimicrobial Agents and Chemotherapy* 37(8):1707–1710 (1994). A bis (monosuccinimide) derivative of p,p'-bis (2-aminoethyl) diphenyl $C_{60}$ showed antiviral activity in human peripheral blood monocular cells (PBMC) acutely infected with HIV, as well as H9 cells chronically infected with HIV, in vitro. No cytotoxicity was shown. It has been suggested that the compound inhibits HIV-1 reverse transcriptase and DNA polymerase $\alpha$.

Fullerenes may also be effective, in addition to their virucidal properties discussed above, as potentiators of existing antiviral agents. Thus, the multiply-substituted fullerene compounds of the invention may be administered for the treatment of viral infections alone or in combination with other therapeutic agents, for example, with other antiviral agents such as 9-(2-hydroxyethoxymethyl)guanine (acyclovir) used to treat herpes viral infections, in particular Herpes Simplex Virus; with 3'-deoxy-3'-azidothymidine (zidovudine) or a 2',3'-dideoxynucleosides (e.g. 2',3'-dideoxycytidine, 2',3'-dideoxyinosine, 2',3'-dideoxyadenosine or 2',3'-dideoxyguanosine), used to treat retroviral infections and in particular HIV infections; interferons (particularly $\alpha$-interferon) and soluble proteins such as CD4, or any other agents such as analgesics or antipyretics which, when in combination with a compound of the invention, provide a beneficial therapeutic effect.

Surprisingly, it has been found that appropriately multiply-substituted fullerenes have substantial and useful biological activity upon various G-protein-linked receptors, certain of which play an etiological role in human disease such as essential hypertension, glaucoma, migraine, and other neurological, endocrine and cardiovascular disorders. This was originally determined when examining scale models of the fullerene structure when displayed upon the same molecular scale as the typical "helical wheel" which represents a two-dimensional rendering of an idealized short segment of alpha helix. In particular, these compounds may be used for the treatment of, inter alia, pain, convulsions, psychosis, neurodegeneration, cerebral ischemia, emesis, cardiovascular diseases (including hypertension) and respiratory disorders, such as asthma.

Fullerenes are ideal in shape and size for use as a template molecule in the design of compounds to be screened for biological activity. Due to their three-dimensional shape, they are already in the right shape for use with biological systems and do not have to fold into an active form as do the peptide chains used in many other combinatorial systems. In addition, the size of the fullerene molecule is appropriate for docking in biological receptor sites. For example, at 7.2 angstroms intermolecular distance, the $C_{60}$ molecule is close in size to many hormones and drugs.

Appropriately multiply-substituted fullerenes can be synthesized which may closely resemble the arrangement, in three-dimensional space, of the sidechain of the amino acid residues which comprise a section of idealized alpha-helical structure. The result is a library of peptidomimetics that contain entities resembling domains of at least two full turns of an alpha helix, two beta turns joined by a 3–5 residue domain, or many other combinations in a defined tertiary structure. Accordingly, such multiply-substituted fullerenes may possess biological activities closely resembling natural peptides, without the disadvantages of peptides, and could therefore be themselves considered as therapeutic agents.

In a preferred embodiment of the invention, three types of substituents are added to the fullerene molecule: a basic group, an acidic group and a neutral group. Using such different groups results in the most diverse libraries. By careful choice of the groups added, it is possible to mimic virtually any desired structure.

Fullerenes also possess numerous desirable biological properties. The toxicology of $C_{60}$ itself closely resembles that of carbon, and substituted fullerenes do not possess carcinogenic or other toxic activities. For example, Nelson et al. have reported, in *Toxicology & Industrial Health,* 9(4):623–30, (1993), that repeated administration of the fullerenes for up to 24 weeks applied in benzene at a dose of 200 ug/day on the mouse skin did not result in either benign or malignant skin tumor formation. No effect on either skin DNA synthesis or ornithine decarboxylase activity was observed over a 72 hour time course after treatment. Zakharenko et al. [Zakharenko et al., *Doklady Akadenii Nauk.* 335(2):261–2 (1994)] have also shown that $C_{60}$ did not produce chromosomal damage at relatively high doses. In addition, a fullerene substituted with peptidomimetic amino-acid sidechain is sufficiently hydrophobic that it can cross cell membranes and, under certain circumstances, can effectively penetrate the blood-brain barrier. This is virtually impossible for peptides larger than two or three residues. Thus, the multiply-substituted fullerenes of the present invention may have utility as carriers of pharmaceuticals or other chemicals, e.g. neurotransmitters, to the brain.

The hydrophobic core of the fullerene can also be used to mimic the hydrophobic nucleus of a molecule, such as a steroid, allowing the technology to be applied to the design of hydrophobic ligands for steroid and growth factor receptors, as well as for modelling more hydrophilic ligands of more ubiquitous pharmaceutical utility.

Each multiply-substituted fullerene compound has a huge number of possible isomers, with each isomer having the functional groups attached at different locations on the sphere. In a preferred embodiment of the present invention, the groups attached to the $C_{60}$ may be thought of as the side chains of alpha-amino acids commonly found in proteins, i.e. basic (B), acidic (A) and neutral (N) groups similar to the side chains of, e.g., lysine, glutamic acid and leucine, respectively. Accordingly, the compound is, in essence, a protein analog.

For example, a tris-adduct having functional groups representing proline, aspartic acid and leucine can be synthesized according to the following scheme:

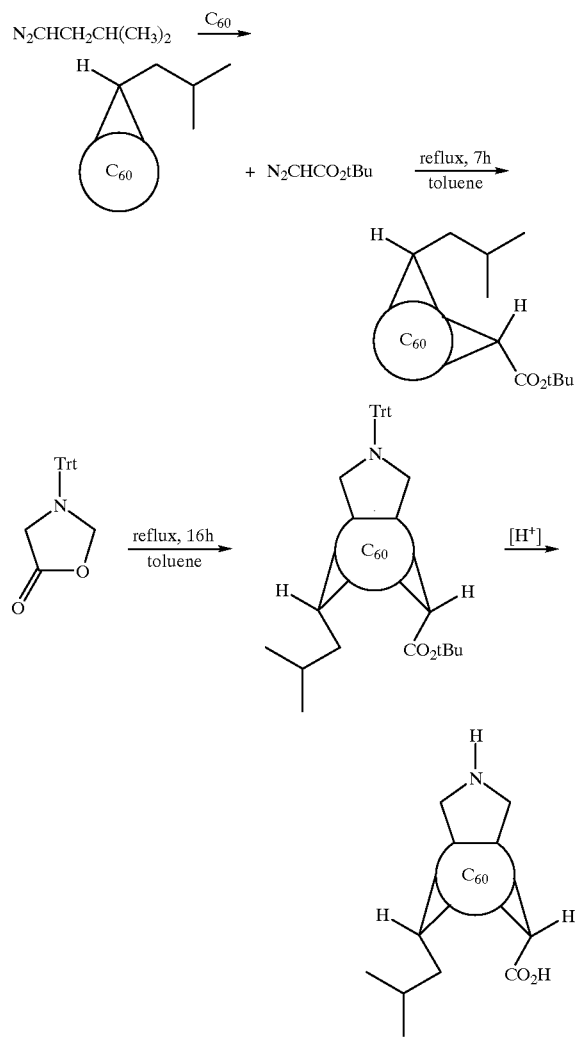

The order of addition of the functional groups and the number added may be varied. Using combinatorial chemistry, a library containing regiosomers and stereoisomers of this trisadduct can be created. Some isomers have proper spatial relationships for biological activity. The library is then screened for those isomers having biological activity.

Thus, the substituted fullerene library contains an enormous number of compounds that are potential drug candidates. These libraries will contain fullerene derivatives that will have moieties attached so as to meet the proper spatial relationship for biological activity.

It has been found that Diels-Alder cycloaddition reactions with fullerenes are sometimes reversible at just above room temperature, depending upon the structure of the diene which has reacted with the fullerene molecule. Also, many aldehydes form unstable adducts with fullerenes which are readily decomposed by moisture or heat. These properties make fullerenes useful for effecting the controlled release of small molecules, such as drugs, from multiply-substituted fullerenes. In a preferred embodiment, the controlled release of active drug substances into the gastrointestinal system, circulatory system, lymphatic system, cerebrospinal fluid, synovial fluid, biliary system, within the aqueous humor of the eye, or in other systems in the body of an animal would be effected in a continuous and constant manner. Such controlled release is highly desirable for the treatment of infectious disease, as well as for the replacement therapy of other diseases caused by deficiencies of, e.g., hormones or enzymes.

Diagnostics and Biosensors

Libraries of multiply-substituted fullerenes may be used for diagnostic purposes. Libraries may be constructed to target cancer cells and deliver imaging agents thereto. In a preferred embodiment, the invention involves labelling fullerenes with a diagnostic agent, preferably an isotope; forming a multiply-substituted fullerene library; screening the compounds of the library for the ability to target tumor cells by standard techniques; separating the compounds having the ability to target tumor cells from cells lacking this ability; administering the compounds having the ability to target tumor cells to the mammal; and utilizing an appropriate imaging method to detect and locate the targeted compounds.

For example, NMR active atoms inside the fullerene will provide a signal for magnetic resonance imaging. Representative NMR active atoms include $^3$He, $^{31}$P, $^{13}$C, $^{11}$B and $^{19}$F. However, any isotope with sufficient energy levels to be detected, and any technique for detecting isotopes in the body, can be used with the claimed method.

Another type of diagnostic agent that is appropriate for use in the claimed method is a fluorescent compound. When a multiply-substituted fullerene containing such a fluorescent compound and having the ability to target tumor cells is administered and exposed to light of an appropriate wavelength, fluorescence will appear in the region of the tumor. Examples of fluorescent dyes which can be used to label fullerene include fluorescein, which appears bright green when exposed to ultraviolet (UV) light; auramine O, which appears yellow when exposed to UV light; and hematoporphyrin and rhodamine B, which appear red upon exposure to UV light. Tumors inside the body can be exposed to light and visualized with this method by utilizing a fiberoptic scope. Image intensifiers and wavelength detectors may be necessary to intensify the image, particularly for small tumors.

Once the labelled fullerenes have proliferated in the area of the tumor, the identity of the tumor can be diagnosed based on the location, shape and size of the region of concentrated labelled fullerenes in the body of the mammal.

The present invention also encompasses the use of fullerene libraries in biosensors. A biosensor is a monitoring device whose selectivity in detecting an analyte is the result of the binding specificity of a biological molecule. Analyte concentrations are determined by "transducing" these analyte binding events into a measurable quantity such as an electronic or optical signal. Thus, the basic components of a biosensor are a biological molecule, e.g., antibody, enzyme or membrane receptor, and a transducer.

Biosensors generally fall into three basic categories: electrochemical, optical or physical. These biosensors incorporate transducers which are well known to the skilled artisan and include calorimetric, piezoelectric, amperometric, optical fiber, optical waveguide, lipid membrane, potentiometric and electrochemical capacitance/impedance devices.

While the aforementioned biosensor transduction techniques and devices may be employed in the invention, future improvements in miniaturization and in other analytical techniques such as mass spectroscopy, gas chromatography and nuclear magnetic resonance spectroscopy may allow such other techniques and systems to be used in the invention.

The biological component of preexisting biosensors is either an enzyme, an antibody, a membrane receptor, whole cell or tissue. Enzymes, antibodies and membrane receptors are all biological macromolecules whose function is to bind target molecules in a highly specific manner. However, it has been found that appropriately multiply-substituted fullerenes having biological activity can be used as the biological component of biosensors. For example, fullerene derivatives capable of specifically binding the analyte of interest may be used. Fullerene derivatives having catalytic activity may also be used in much the same way enzymes are used in existing biosensors. Coating the sensor surface with libraries as either a mixture or in a spacially addressable manner or covalently attaching libraries to the surface leads to improved optimization of biosensor design.

Material Science Applications of Pullerene Libraries

Libraries of multiply-substituted fullerene derivatives are also useful for the desirable electrical, mechanical, optical or electronic properties of the individual compounds therein. Such materials may be formulated from purified library components or mixtures of such components. Fullerene libraries improve the process of discovering new materials by providing rapid access to large numbers of new fullerene molecules whose properties are unusual and desirable. Fullerenes show great promise in materials science because of their (1) unusual redox properties; (2) unique HOMO-LUMO gap; and (3) UV-VIS chromophoric properties. They also are very thermally stable.

Materials science applications of fullerenes have been extensively studied. This research has been reported in *novel Forms of Carbon* (1992) Vol. 270, Renchler et al., eds.; *Science & Technology of Fullerene Materials* (1995), Bernier et al., eds.; and *Fullerenes: Recent Advances in the Chemistry and Physics of Fullerenes and Related Materials* (1994), published by The Electrical Society. The contents of these publications are hereby incorporated by reference.

Typical uses of fullerene libraries are the construction of novel electronic devices including batteries, fuel cells, display and memory-storage devices, etc. Fullerene libraries can be shaped into a pellet or deposited on a stainless steel disk to serve as an electrode. Fullerene libraries of the invention are also useful for fabrication of nano-materials, construction of light-emittihg devices, production of composites, preparation of energetic materials and storage of energy.

Thin films of fullerene libraries can be rapidly produced by combining the multiply-substituted fullerene compounds of the claimed invention with a lipid. The resulting monolayers and bilayers have many uses in, e.g., electronic devices, optoemissive devices and chemical sensors. For example, multiply-substituted fullerenes in a lipid bilayer system produce very large photocurrents and thus can be used for trans-membrane electron-transport in an artificial photosynthetic energy storage device. Such a system can be constructed according to the method of Hwang et al., in *Fullerenes: Recent Advantages in the Chemistry and Physics of Fullerenes and Related Materials* (1994), 845–851.

Multiply-substituted fullerenes may be used to produce materials with superconductive properties, including materials which exhibit such behavior regardless of the critical temperature and pressure. Metals such as K, Rb and Cs can be added to multiply-substituted fullerenes to form high temperature superconductors. The most preferred form has the formula $C_{60}M_3$.

Fullerene libraries can also be used for catalysis research since fullerenes and fullerene derivatives are known to be excellent ligands for transition metals such as nickel, palladium, platinum, ruthenium and iridium. Catalyst formulations for polymerization, oxidation & hydroformylation can be prepared by addition of suitable metals to fullerene libraries. In particular, the use of fullerenes as catalysts for reactions such as methane activation, carbon-carbon bond cleavage and trans-hydrogenation has been studied [Wu et al., *Fullerenes: Recent Advances in the Chemistry & Physics of Fullerenes and Related Materials* (1994) 758–767].

Donor-acceptor complexes of fullerene libraries of the present invention can be made as by mixing donor molecules such as aromatic amines with the libraries. Useful optical properties can be decoded for certain compounds in the libraries by analysis of sublibraries.

Fullerene libraries of the present invention can also be used as reagents, in particular for organic synthesis, polymer-assisted synthesis and catalysis.

Fullerene libraries of the present invention can be used in preparation of materials such as polymers, sol-gels or ceramics as well. Components of the libraries are excellent for basic building blocks in high strength materials applications. For example, multiply-substituted fullerenes in aqueous solution can be added to a solution of melamine and formaldehyde, and copolymerized at acidic pH and 45° C. over a four day period (according to the method of Bell et al., in *Fullerenes: Recent Advances in the Chemistry & Physics of Fullerenes & Related Materials* (1994) 92–106]. The resulting gel is an organic xerogel having a low specific surface area.

The multiply-substituted fullerenes of the claimed invention can be used to prepare polymers wherein the fullerene is either in the chain or off the chain. Suitable methods of preparation are taught by Belik et al. in *Fullerenes: Recent Advances in the Chemistry & Physics of Fullerenes & Related Materials* (1994) 701–712.

Regioselectivity of Substituted Fullerenes

Multiple approaches may be taken towards masking of one portion of the fullerene "ball" in order to limit reactivity of the available portion to a given reagent. First, $C_{60}$ can function in the Diels-Alder reaction as a dieneophile or itself as a diene. Retro-Diels-Alder reactions with hindered dienes are thermally relatively facile, and occur at relatively low temperatures (100–120° C.). Thus one or more successive reactions with a diene can be used to sterically restrict the amount of fullerene surface which is unhindered for reaction with a different reactant. Such an approach can be used to prepare a single regioisomer as desired.

Additional approaches might use the relatively stable pi-complexes that $C_{60}$ is well known to form with a variety of substances, such as porphyrins, and electron-rich extended aromatic systems. Less work of this nature has been disclosed; however, enough is known to suggest that optimization of this scheme would result in a system in which regioisomer formation could be carefully controlled.

Fullerenes are also known to form quite stable Van der Waals complexes, for example with cyclodextrins. The use of appropriate cyclodextrins would allow regioselective a derivatization to take place.

Formulation of Cosmetics and Other Controlled Release Products with Fullerene Libraries The timed release and controlled release of perfumes, moisturizers, pigments and other desirable components of cosmetics formulations can be improved by the use of fullerene libraries. For example, addition of the salt of perfume components to $C_{60}$ yields an adduct that is stable at room temperature, but slowly releases the desirable volatile component by desorption.

The potential for controlled release of a small molecule from multiply-substituted fullerenes, discussed supra, may be utilized in the formulation of other useful compositions as well. Among these are: the controlled release of insect pheremones from preparations which are used for the agricultural control of insect pests; of insect anti-feedants for the same purpose; of potent toxins for use in rodenticides; and of a molluscacidal agent (such as an α, β unsaturated ketone) from paints or coatings to be applied to the surfaces of ships, piers or other marine structures.

Illustrative Naming Scheme for Multiply Substituted Positional Isomers of $C_{60}$ The naming of specific fullerene ($C_{60}$) isomers is complex. No standard scheme as sanctioned by the International Union of Pure and Applied Chemistry ("IUPAC") for such nomenclature has been established. However, several systems have been proposed.

The two most common systems are shown in FIG. 1 [the "Taylor Scheme"; c.f. Taylor et al., *Pure and Applied Chemistry*, 65(1):135–142 (1993)] and FIG. 2 [the "Hirsch Scheme"; c.f. Hirsch et al., *Angew. Chem. Intl. Ed.*, 33(4):437–438 (1994)].

Not counting stereochemistry there are eight possible bis-isomers possible at the 6/6 carbon bonds only.

| Hirsch | Taylor | Number of Stereoisomers |
|---|---|---|
| cis-1 | 1,2,3,4 | 4 |
| cis-2 | 1,2,7,21 | 4 |
| cis-3 | 1,2,16,17 | 4 |
| equatorial | 1,2,18,36 | 4 |
| trans-4 | 1,2,34,35 | 4 |
| trans-3 | 1,2,33,50 | 4 |
| trans-2 | 1,2,51,52 | 4 |
| trans-1 | 1,2,55,60 | 1 |

Note:
Because $C_{60}$ primarily reacts at the 6/6 bonds shown above the minor products from the reaction at the 6/5 center are not named.

Products from addition to $C_{60}$ at the most reactive 6/6 bond are of two types. The addition of XY gives the two compounds of FIG. 2 while the addition of $X_2$ or a symmetric group X gives one type of adduct as shown in FIG. 3.

Figure 4:
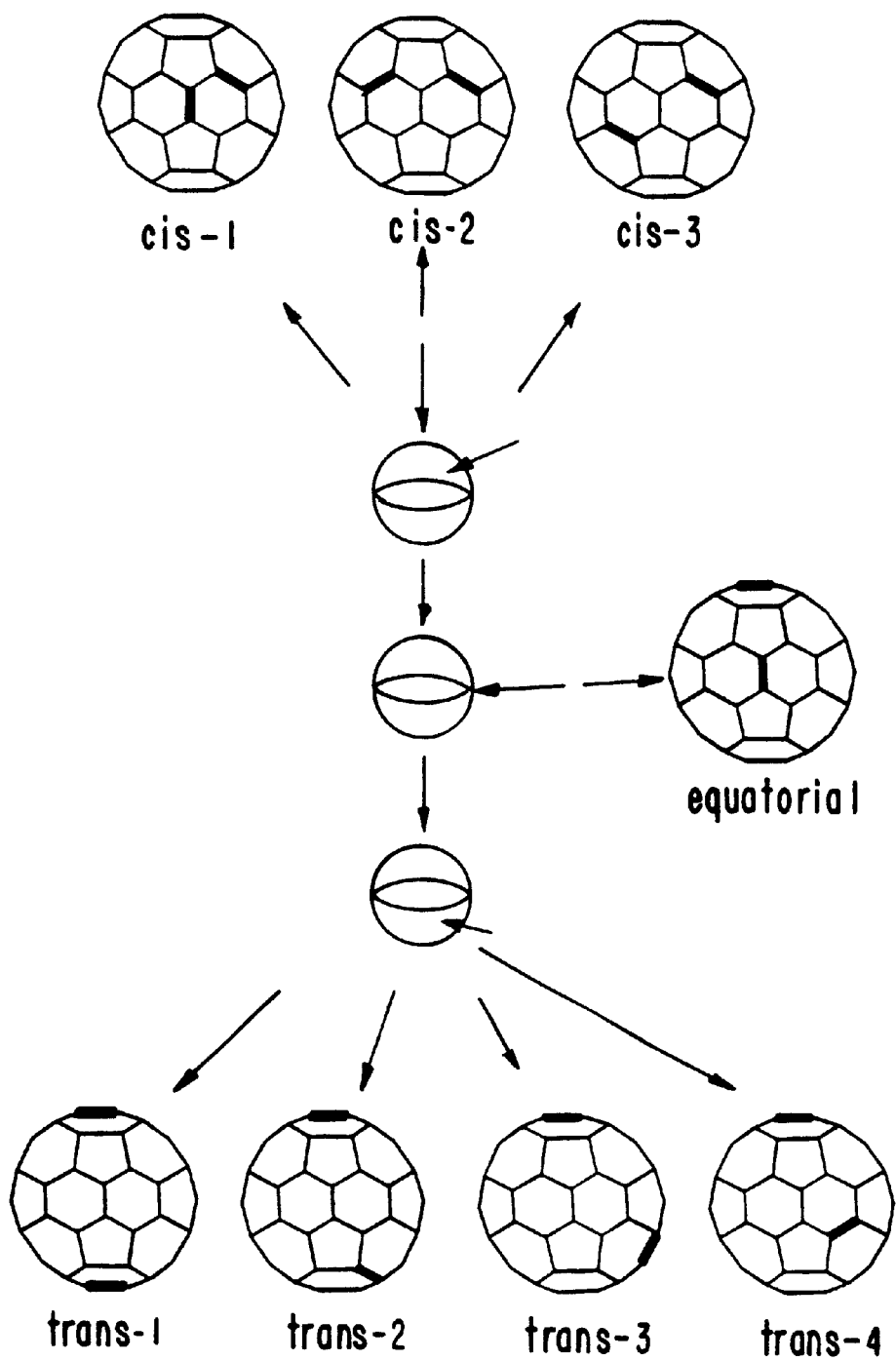
FIG. 4 is a schematic illustration of the bisadducts formed by addition to $C_{60}$.

Thus, reactions at the 30 double bonds of $C_{60}$ give 29×28=812 products or 29×1=29 products depending upon the nature of the substituent. FIG. 4 shows the positioned relationships between the 6/6 bonds in $C_{60}$ and the corresponding bisadducts in the "Hirsch Nomenclature."

Figure 5:
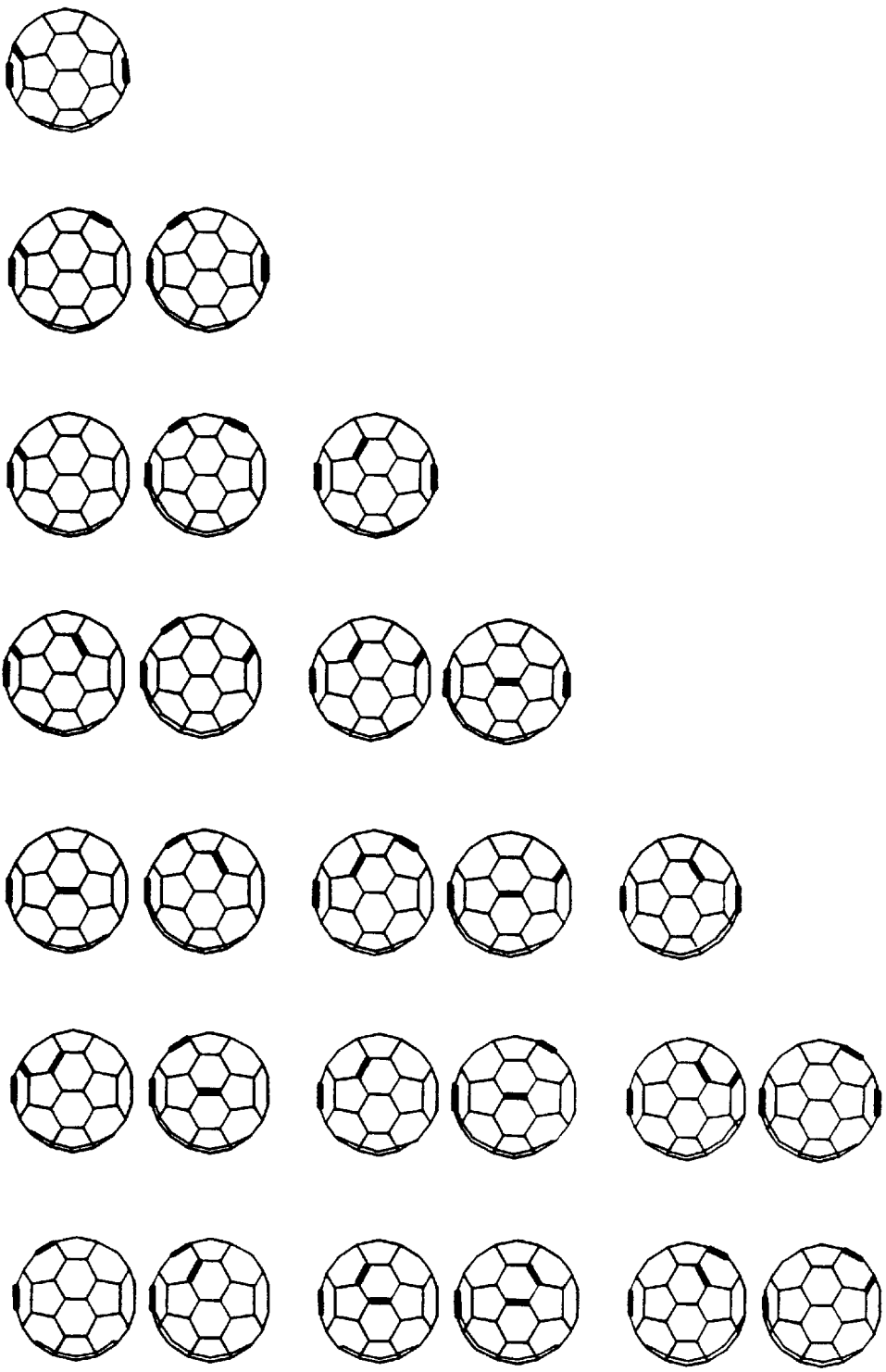
FIG. 5 is a schematic illustration of the tris adducts formed by addition to $C_{60}$.

The reaction of $C_{60}$ to form tris isomers, $C_{60}+X_1Y_1+X_2Y_2+X_3Y_3 \rightarrow [C_{60}](X_1Y_1)(X_2Y_2)(X_3Y_3)$ leads in the symmetric case (where $X_n=Y_n$) to 42 products not counting stereochemistry. FIG. 5 shows a selected group of 28 isomers in the "Hirsch Nomenclature" as seen from the front side. These compounds are named as:

cis-1/cis-2
cis-1/cis-3
cis-1/equatorial
cis-1/trans-4
cis-1/trans-3
cis-1/trans-2
cis-1/trans-1
cis-2/cis-2
cis-2/cis-3
cis-2/equatorial
cis-2/trans-4
cis-2/trans-3
cis-2/trans-2
cis-2/trans-1
cis-3/equatorial
cis-3/trans-4
cis-3/trans-3
cis-3/trans-2
cis-3/trans-1
equatorial/trans-4
equatorial/trans-3
equatorial/trans-2
equatorial/trans-1
trans-3/trans-2
trans-3/trans-1
trans-4/trans-3
trans-4/trans-2
trans-4/trans-1

Figure 6:
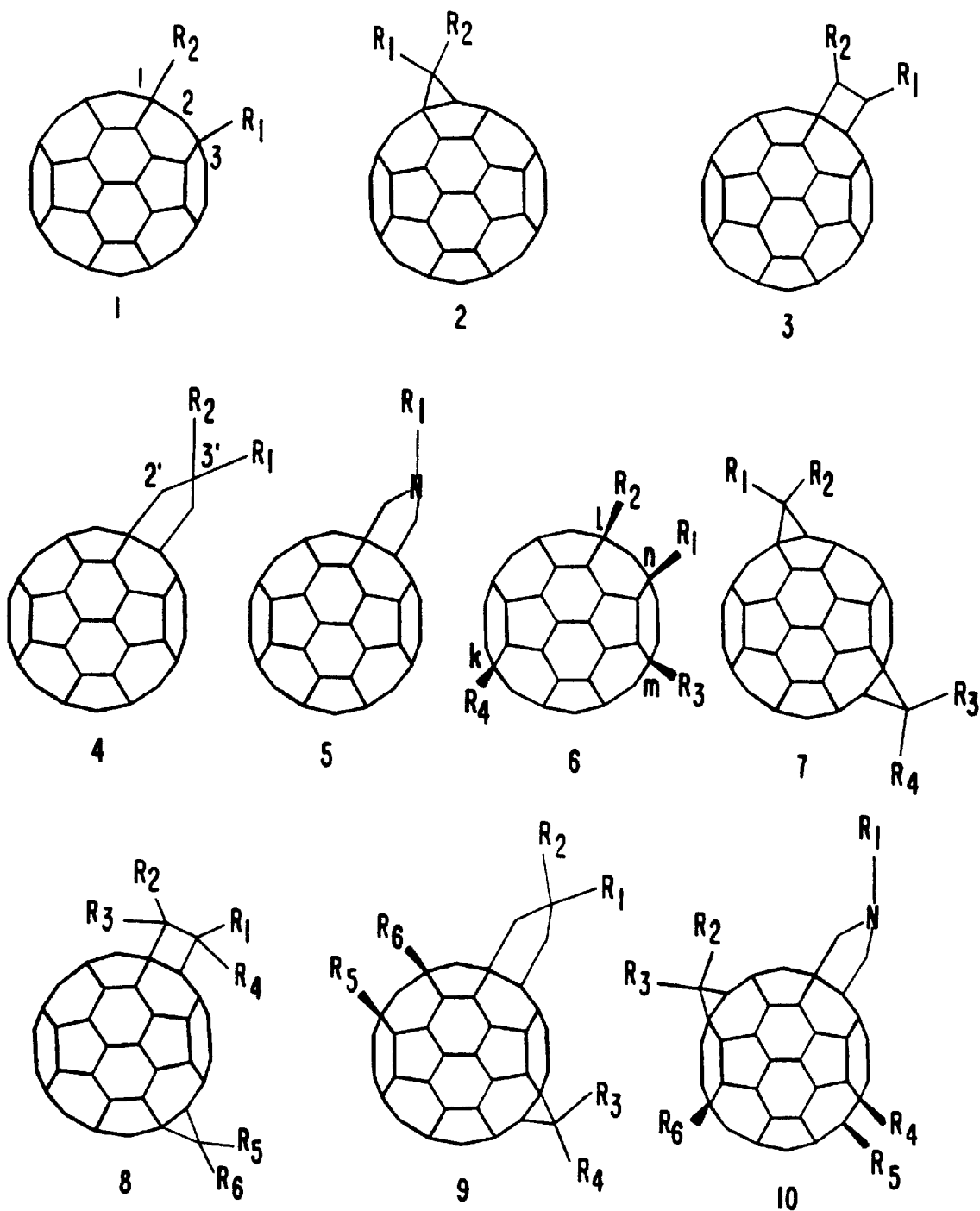
FIG. 6 is a schematic illustration of representative substituted fullerenes.

According to the nomenclature developed herein, the structures in FIG. 6 wherein $R_1$ and $R_2$ are alkyl would be denoted as (1,n)-dialkyl-$C_{60}$, wherein n is an integer from 1 to 60 which defines the position of substitution upon the $C_{60}$ structure. For example, Structure 1 in FIG. 6 would be named (1,3)-dialkyl-$C_{60}$. Structure 2 would be named as 1,2-dialkyl-cyclopropa-$C_{60}$. Structure 3 would be named as 1,2-cyclobuta-(1,n)-$C_{60}$. Structure 4 would be named as (3,3')-dialkyl-cyclopenta-$C_{60}$. Structure 5 would be named as (1,2)-3'-alkyl-(1,2)-azacyclopenta-$C_{60}$. Structure 6 would be named as (1,n,m,k)-tetraalkyl-$C_{60}$ wherein n, m and k can independently be integers from 2 to 60. Structure 7 would be named as a bis-1',1'-dialkyl-1'',1''-dialkyl-[cyclopropa]-(1,2,n,k)-$C_{60}$. Structure 8 would be named as 1',1'-dialkyl-cyclopropa-(1,2)-2',2'-dialkyl-3',3'-dialkyl-(m,k)-cyclobuta-$C_{60}$. Structure 10 would be named as (1,n,m)-trialkyl-(1',1')-(k,p)-[cyclopropa]-(q,r)-3-alkyl-azacyclopenta-$C_{60}$ wherein n, m, k, l, p, q and r are independently integers from 1 to 60.

In all these examples, R=alkyl is a nonlimiting example.

Identification and Isolation of Multiply-Substituted Fullerene Derivatives

A method using $^3$He NMR has been developed for the analysis and characterization of isomers and determination of regioselectivity. A $^3$He label can be introduced into $C_{60}$ by using high pressure and heating to obtain $^3$He-labeled $C_{60}$, which is used to obtain the first $^3$He-NMR spectrum of helium compounds. By heating the fullerene under pressure, a "window" is opened in the fullerene molecule and a helium atom is trapped inside. (Only a trace (0.1%) of the fullerene molecules are labeled with the helium isotope, but this is sufficient for the present purpose.) The helium nucleus inside the fullerene compound "feels" a different magnetic field, depending on the structure of the surrounding compound. Thus, because the helium is inside the fullerene molecule, the $^3$He NMR spectrum is characteristic of the position and number of the groups attached to the outside of the fullerene molecule. Each helium-labeled fullerene gives a single sharp peak since reactions at different sites alter the pi bonding structure of the fullerene to produce substantial shifts in the $^3$He peak.

A method for the identification of groups attached to the fullerene molecule using electrospray mass spectrometry has also been developed. Electrospray, or ion spray, mass spectrometry can be used to characterize the diversity and structures of fullerene libraries.

Analysis of fullerene libraries by electrospray is carried out both manually and using robotic autosampler/HPLC/MS. If only a few libraries are to be analyzed, the library mixture is dissolved in a suitable solvent such as 1:1 benzene-methanol, THF, $CH_2Cl_2$ acetonitrile or pure methanol. The sample is infused into the instrument using a Sage syringe pump. Typical sample flow rates are 2–4 ml/min. If necessary, the fullerenes can be tagged with suitable reagents such as a diazo crown ether. Data is collected with a Teknivent Vector One data system, processed and plotted.

Figure 7:
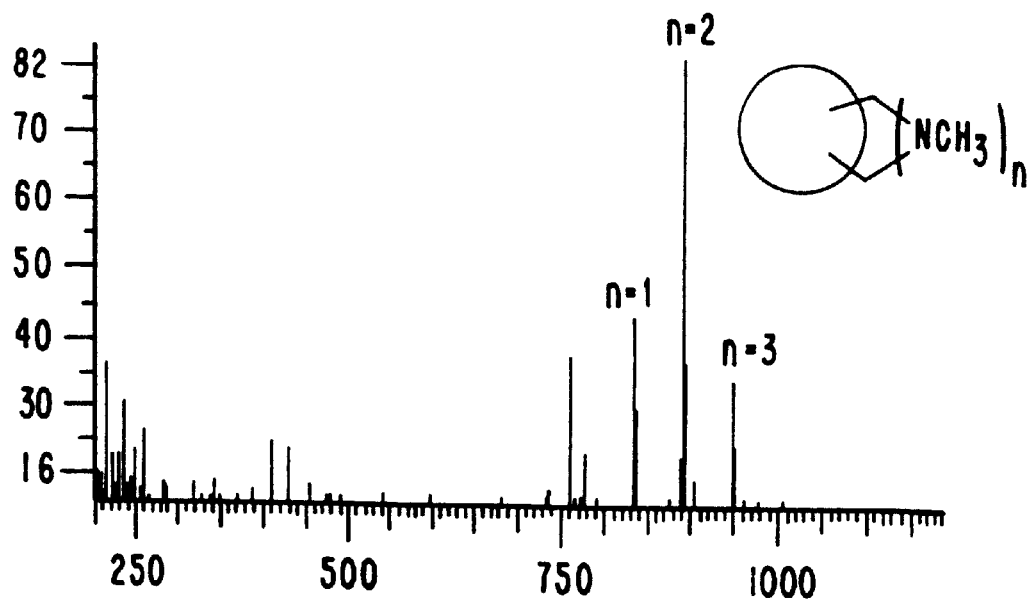
FIG. 7 is the electrospray mass spectrum of a fullerene library prepared by addition of an excess of sarcosine and paraformaldehyde to $C_{60}$.

For example, a solution containing the fullerene library prepared by addition of an excess of sarcosine and paraformaldehyde to $C_{60}$ was infused into the electrospray source of a Vestec Model 201 instrument to obtain the spectrum shown in FIG. 7.

Figure 8:
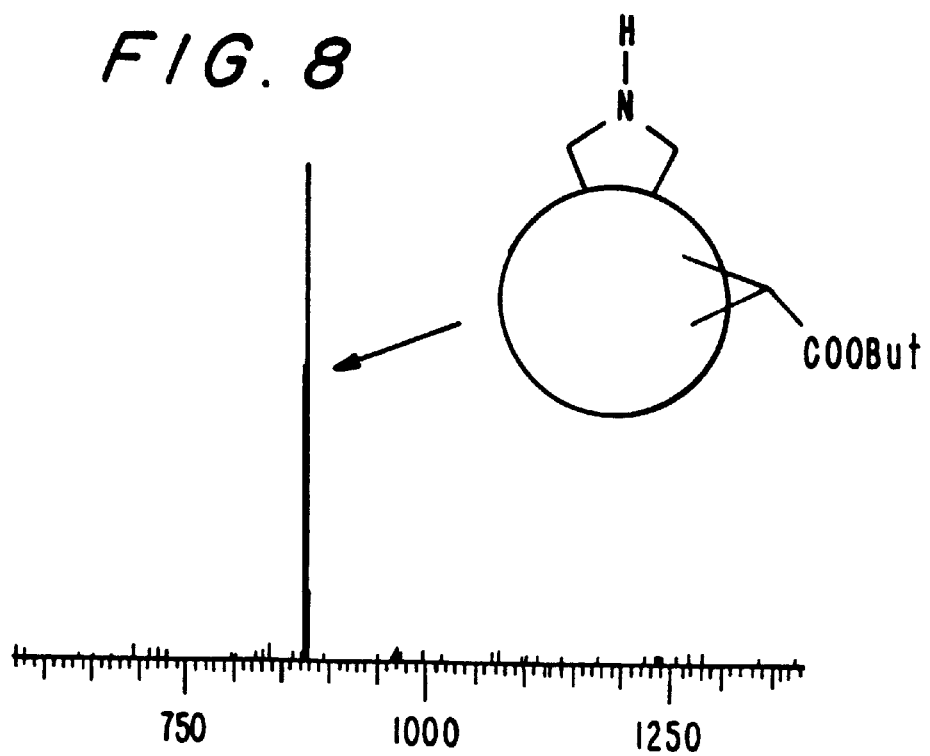
FIG. 8 is the electrospray spectrum of a fullerene library prepared by addition of an excess of N-triphenyl methyloxazolidone and t-butyldiazoacetate in toluene.

FIG. 8 shows the electrospray spectrum of a fullerene library with two different groups attached. The spectrum shows a molecular ion consistent with addition of the amino and protected carboxyl group as shown in the figure.

In each case the peak shown represents the molecular weight of the fullerene library component or components.
Screening of Combinatorial Libraries for Multiply-Substituted Fullerene Derivatives Having Biological Activity Methods have been developed for determining and screening those substituted fullerene derivatives that have biological activity. Well-known methods of measuring the binding affinity of biologically active molecules can be used to screen libraries of multiply-substituted fullerene compounds.

Compound libraries are screened for biological activity by means of receptor binding assays or in vitro physiometric assays. In a preferred embodiment, solid-phase receptor binding assays are performed using a cloned receptor. The cloning of G-protein linked receptors is well known to those skilled in the art, and indeed cloned receptor preparations corresponding to the dopamine $D_1$, $D_2$, $D_3$, $D_4$ and $D_5$, the 5-HT-1A, 5-HT-2, 5-HT-1B, and other serotonin receptor subtypes, the muscarinic M1, M2, M3, M4 and M5 receptors, the neuropeptide NPY-1 receptor, the NPY-2 receptor, and many others are commercially available. Typically, the cloned receptor preparation is incubated in 96-well plates at a concentration of less than 100 micrograms of membrane protein per milliliter with $[H^3]$-labeled radioligands appropriately specific for the receptor subtype. Included in some of the wells of these plates are compounds which are members of the compound libraries which are desired to be screened for biological activity. After filtration of the contents of the various wells through a cell harvester, washing of the filters to remove excess unbound tritiated activity, and counting in a liquid scintillation counter it is possible to determine if any of the members of the compound libraries possess biological activity which is of potential therapeutic utility.

In another preferred embodiment natural tissue homogenates would be utilized as the source of receptor rather than using cloned receptors. This has the disadvantage that many different receptors may be present in a natural tissue homogenate, but has the advantage of lower cost. Typically, the receptor preparation is incubated in 96-well plates at a concentration of less than 300 micrograms of membrane protein per milliliter with $[H^3]$-labeled radioligands appropriately specific for the receptor subtype. Included in some of the wells of these plates are compounds which are members of the compound libraries which are desired to be screened for biological activity. After filtration of the contents of the various wells through a cell harvester, washing of the filters to remove excess unbound tritiated activity, and counting in a liquid scintillation counter it is possible to determine if any of the members of the compound libraries possess biological activity which is of potential therapeutic utility.

In vitro physiometric assays involve examination of the physiological response of a strip of tissue perfused with isotonic salt solutions to the applications of various pharmacologically active agents. Typically, the tissue is suspended in such a bath containing the oxygenated salt solution maintained at 34–37° C. by means of a suture or similar ligature which is connected to a displacement transducer. The output of this displacement transducer is connected to a polygraphic recorder, computer, or similar device that allows the dynamic displacement behavior experienced by the tissue in response to the various pharmacological agents to be recorded. Members of compound libraries can then be added to the tissue bathing medium either at the same time, just before, or just after a peptide, drug or other agent is similarly added to the bath. Therefore, by methods well known to those skilled in the art, it is possible to determine the $IDS_{50}$ value for a particular library member, the $ED_{50}$ for such a member, or the Schild constant $K_s$ or more usually its negative logarithm $pK_s$, all of which serve to characterize the pharmacological potency of a member of a compound library as compared with a drug or agent of known potency.

When activity is picked up in an assay, a modified library will be screened. Controlled library synthesis will be conducted omitting reagents and at various time stages in order to deduce the structure of the specific active isomer. Bioassay guided concentration of the active intermediate and isolation of the pure isomer is accomplished using HPLC. Identification and specific synthesis would follow.
Preparation of Fullerene Libraries In general, the combinatorial chemistry reagents are used in sufficient quantities in the following examples to completely convert the starting materials to products, but to be themselves substantially consumed during the course of the reaction. However, the amounts may be varied. For example, in a reaction of two compounds, one of which is not readily available and one of which is, an excess of the readily available compound may be used to drive the reaction further towards completion (unless the use of an excess would increase the synthesis of an undesired compound).

Protecting groups may also be used in the combinatorial synthesis of the substituted fullerenes. These are groups which are chemically bound to a moiety, capable of protecting that moiety from extraneous reactions, and which may be removed upon selective exposure to an activator, e.g. an acidic or basic environment, or to electromagnetic radiation and, especially light, such as ultraviolet and visible light. Examples of protecting groups useful for the claimed invention include t-butoxycarbonyl, fluorenylmethyloxycarbonyl, trityl, nitropiperonyl, pyrenylmethoxycarbonyl, nitroveratryl, nitrobenzyl, and other orthonitrobenzyl groups, dimethyl dimethoxybenzyl, 5-bromo-7-nitroindolinyl, o-hydroxy-α-methyl cinnamoyl, and 2-oxymethylene anthraquinone.

Most of the temperature ranges given in the following examples are merely exemplary, and it is within the ability of one of ordinary skill in the art to vary those that are not critical.

Likewise, the reaction times set forth in the examples are also merely exemplary and may be varied.

Generally, each reaction is monitored, e.g., by thin layer chromatography, and is terminated when at least one starting material is no longer detectably present, or when it appears that no more of the desired product is being formed.

The product of each reaction may, if desired, be purified by conventional techniques such as recrystallization (if a solid), column chromatography, preparative thin layer chromatography, gas chromatography, fractional distillation under high vacuum or high pressure (performance) liquid chromatography (HPLC). Often, however, the crude product of one reaction may be employed in the following reaction without purification or even without isolation.

Some reactions, particularly those utilizing strong bases or reducing agents, require anhydrous solvents. Where this is the case solvents may be dried before use using conventional techniques and an inert atmosphere.

In the following examples, organic solutions were dried over sodium sulfate or magnesium sulfate, and evaporated under reduced pressure. NMR spectra were recorded at ambient temperature in deuteriochloroform. All chemical shifts are given in parts per million relative to tetramethylsilane. Infrared spectra were recorded at ambient temperature in solution in chloroform, or in the solid state in a potassium bromide disc as noted.

Chromatography was carried out by flash using silica gel.

Definitions

For purposes of clarity, the terms and phrases used throughout this specification and the appended claims are defined in the manner set forth directly below.

The symbols

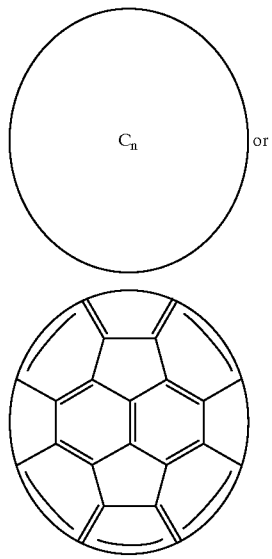

represent a fullerene molecule having n carbon atoms.

The term "solvent" includes mixtures of solvents and implies that the reaction medium is a liquid at the desired reaction temperature. It should, therefore, be understood that not all of the solvents listed for a particular reaction may be utilized for the entire cited temperature range. It should also be understood that the solvent must be at least substantially inert to the reactants employed, intermediates generated and end products under the reaction conditions utilized.

The term "inert atmosphere", as utilized herein, means an atmosphere that does not react with any of the reactants, intermediates or end products or otherwise interfere with the reaction. While a carbon dioxide atmosphere is suitable for certain reactions, the inert atmosphere is usually nitrogen, helium, neon, or argon, or a mixture thereof, and most often dry argon to maintain anhydrous conditions. Most reactions, including those where the use of an inert atmosphere is not specified, are carried out under an inert atmosphere, usually dry argon, for convenience.

The term "substituted," as used herein with reference to fullerenes, means the addition of atoms or groups of atoms to the fullerene molecule. When used herein with reference to other molecules, the term "substituted" means that an one or more hydrogen atom(s) on the designated molecule is replaced with another atom or group of atoms provided that the designated atom's allowed valencies are not violated, and that the substitution results in a stable compound.

The term "alkyl" means a straight or branched chain hydrocarbon group containing no unsaturation and having from 1 to 22 carbon atoms. "Lower alkyl" means a hydrocarbon groups having from 1–6 carbon atoms, while "higher alkyl" means a hydrocarbon group having from 7 to 22 carbon atoms. Preferred lower alkyl groups include methyl, ethyl, propyl, isopropyl and t-butyl.

The term "cycloalkyl group" means a cyclic alkyl group having from 3 to 12 carbon atoms. The cycloalkyl may have substituents such as amino (which may be substituted by an acyl, halogen, aryl, phenyl and/or alkyl), halogen, nitro, sulfo, cyano, hydroxy, carboxyl, oxo, thioxo, $C_{1-22}$ alkyl (which may be substituted by an aryl, halogen, amino, hydroxy, carboxyl, alkoxy, alkylsulfonyl and/or dialkylamino), cycloalkyl, alkoxy (which may be substituted by a halogen and/or hydroxy), acyl having one to four carbon atoms, aryl (which may be substituted by a halogen, nitro, alkyl, alkoxy, amino, sulfo, hydroxy and/or cyano) or oxo or the like.

The term "alkenyl" means a straight or branched chain hydrocarbon group containing a carbon to carbon double bond and having from 3 to 22 carbon atoms.

The term "alkynyl" refers to a straight or branched chain hydrocarbon radical containing unsaturation in the form of a carbon to carbon triple bond and having from 3 to 22 carbon atoms.

The term "aryl" shall mean phenyl or phenyl substituted by one or more substituents such as chloro, bromo, fluoro, $C_{1-8}$ alkyl, $C_{1-8}$ alkoxy, nitro, hydroxy, primary or secondary amine, amino acid sidechain, or trihalomethyl.

As used herein, the term "heterocycle" or "heterocyclic group" is intended to mean a stable 5- to 7-membered monocyclic or bicyclic or 7- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Preferred heterocycles include 2-pyridyl, 3-pyridyl, 4-pyridyl, pyrimidyl, pyrazinyl, pyridazinyl, pyrazolyl, benzopyranyl, quinolyl, thieno[2,3-b]pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, thiophene, piperidyl, piperidino, piperazinyl, dioxolane, and morpholino. Most preferred heterocycles include pyridyl, dioxolane, and thiophene.

The "heterocyclic groups" may have substituent(s) such as an amino (which may be substituted by an acyl, halogen, aryl, phenyl and/or alkyl), halogen, nitro, sulfo, cyano, hydroxy, carboxyl, oxo, thioxo, $C_{1-22}$ alkyl (which may be substituted by an aryl, halogen, amino, hydroxy, carboxyl, alkoxy, alkylsulfonyl and/or dialkylamino), cycloalkyl, alkoxy (which may be substituted by a halogen and/or hydroxy), acyl having one to four carbon atoms, aryl (which may be substituted by a halogen, nitro, alkyl, alkoxy, amino, sulfo, hydroxy and/or cyano) or oxo or the like. Preferred substituted heterocyclic groups are 5-methoxy-indole, 5-chloro-2-pyridyl, 3-methoxy-2-pyridyl, 5-methyl-2-benzothiazolyl, 5-methyl-4-phenyl- 2-thiazolyl, 3-phenyl-5-isoxazolyl, 4-(4-chlorophenyl)-5-methyl-2-oxazolyl, 3-phenyl-1,2,4-thiadiazole-5-yl, 5-methyl-1,3,4-thiadiazole-2-yl, 5-acetylamino-2-pyrimidyl, 3-methyl-2-thienyl, 4,5-dimethyl-2-furanyl, and 4-methyl-2-morpholinyl.

The term "amine" is intended to mean a compound in which one or more of the hydrogen atoms of an ammonia molecule have been substituted by an organic group. A "primary amine", as used herein, in an amine having the formula $RNH_2$, wherein R represents any organic group. A "secondary amine" is an amine having the formula $RR'NH_2$, wherein R and R' represent organic groups which may be the same or different.

The term "amino acid residue" refers to an amino acid formed upon cleavage of a polypeptide at its peptide linkages. "—NH" refers to the free amino group present at the amino terminus of a polypeptide. "—COOH" refers to the free carboxyl group present at the carboxyl terminus of a polypeptide. Standard polypeptide nomenclature described in *J. Biol. Chem.*, 243:3552–59 (1969) and adopted at 37 C.F.R. 1.822(b)(2), is used herein.

In addition, the phrase "amino acid residue" is broadly defined to include any modified and unusual amino acid, including, but not limited to, those listed in 37 C.F.R. 1.822(p)(2), which is incorporated herein by reference. Furthermore, it should be noted that a dash at the beginning or end of an amino acid residue sequence indicates either a peptide bond to a further sequence of one or more amino acid residues or a covalent bond to a carboxyl or hydroxyl end group.

The term "amino acid side chain" means a characteristic side chain attached to the —$CH(NH_2)(COOH)$ moiety in any amino acid residue.

The term "animal" as used herein includes mammals and nonmammals, and further includes humans and non-human mammals.

The phrase "$EC_{50}$ concentration" as used herein means that concentration of a compound or drug which is necessary to elicit a 50% maximal biological response, i.e. that which is necessary to elicit a 50% reduction in the contractions of guinea pig ileum segments in a prostaglandin antagonism assay.

The phrase "$ED_{50}$ dose" as used herein means that dose of a compound or drug which produced a biological effect, such as producing analgesia, in 50% of the animals to which the compound or drug was administered.

The terms "halo" and "halogen" as used herein mean chlorine (Cl), bromine (Br), fluorine (F) and/or iodine (I).

The phrases "parenteral administration" and "administered parenterally" as used herein mean modes of administration other than enteral and topical administration.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with suitable base. Representative salts include hydrochloride, hydrobromide, sulfate, bisulfate, acetate, valerate, oleate, palmitate, stearate, laurate, benzoate, lactate, oxalate, phosphate, nitrate, tosylate, citrate, maleate, fumarate, succinate, trialkylammonium, tartrate, napsylate, and clavulanate salts; alkali metal salts, such as lithium, sodium and potassium; and alkaline earth salts, such as calcium and magnesium. Other pharmaceutically acceptable salts will be readily apparent to one skilled in the art.

The phrase "N-protecting group" or "N-protected" as used herein means those groups intended to protect the N-terminus of an amino acid or peptide, to protect an amino group against undesirable reactions during synthetic procedures.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio.

EXAMPLES

The following examples illustrate but do not limit the scope of the invention disclosed in this specification.

Example 1

Synthesis of N-tritylglycine

N-tritylglycine was prepared in 90% yield from trityl chloride and glycine according to the procedure of Zervas et al., *J. Am. Chem. Soc*, 78:1359 (1956).

Example 2

Synthesis of N-triphenylmethyloxazolidone

In a 500 mL three-necked roundbottom 24/40 flask equipped with nitrogen inlet, graduated pressure-equalizing addition funnel, and magnetic stirrer was added 1.056 gm (3.327 mMol) of tritylglycine and 78 mL of absolute ethanol. Upon solution of the tritylglycine, 1.55 mL of 37% (w/v) aqueous formaldehyde (formalin) in 30 mL of 95% ethanol was added dropwise over a period of two hours, at room temperature. At the end of this period, the mixture was evaporated to dryness on a Buchi rotary evaporator at 30° C. under mechanical pump vacuum (approximately 50 microns pressure). The residue was taken up in 155 mL of dichloromethane, dried over anhydrous $MgSO_4$, and evaporated in the rotary evaporator as above to yield crude crystalline material. This was recrystallized from warm methanol to give 1.090 gm of pure crystalline material.

Example 3

Synthesis of N-trityl(azacyclopentano)-[1,2]-buckminsterfullerene by Dipolar Cycloaddition of N-triphenylmethyloxazolidone to $C_{60}$ In a 500 mL three-necked round bottom 24/40 flask equipped with nitrogen inlet, reflux condenser, and magnetic stirrer was added 252.6 mg (0.766 mMol) of N-triphenylmethyloxazolidone in 163 mL of toluene. To this solution under nitrogen was added 502.3 mg (0.697 mMol) of chromatographically purified $C_{60}$ (MER, Tucson, Ariz.). Upon thorough mixing of the solutions under nitrogen, the solution was heated under reflux and nitrogen for a 16-hour period. At the end of this time, solvent was removed on a Buchi rotary evaporator at 30° C. under mechanical pump vacuum (approximately 50 microns pressure). The dark-colored residue was purified by flash chromatography on chromatographic grade silica using as eluting solvent a 1:1 (v/v) mixture of toluene and hexanes. Pooling of approximate fractions followed by removal of solvent as above yielded 103 mg (76%) of chromatographically pure product. Electrospray mass spectrum: Single peak at (1006.06+Na$^+$).

Example 4

Synthesis of 1-carboxy-cyclopropane-[1,2]-buckministerfullerene t-butyl ester and bis{1-carboxy-cyclopropane}-[1,2], -[n,m]-buckministerfullerene t-butyl ester These compounds were prepared essentially according to the procedure outlined in Isaacs et al., *Helv. Chem. Acta* 76:1231 (1993). In a 500 mL three-necked roundbottom 24/40 flask equipped with nitrogen inlet, reflux condenser, and magnetic stirrer was added 69 mg (0.486 mMol) of t-butyl diazoacetate (obtained in 70% yield by saponification of t-butylazidbacetoacetate with sodium methoxide, and the t-butylazidoacetoacetate obtained by the procedure given in *Organic Synthesis,* Collective Vol. 5, p. 179 (1973) and 100 mL of toluene. To this solution was then added 250 ml of a toluene solution of 350 mg (0.486 mMol) of $C_{60}$. The mixture was heated under reflux and under a stream of nitrogen for a seven-hour period. At then end of this time, solvent was removed on a Buchi rotary evaporator at 30° C. under mechanical pump vacuum (approximately 50 microns pressure). The dark-colored residue was purified by flash chromatography on chromatographic grade silica using as eluting solvent a 1:1 (v/v) mixture of toluene and hexanes. Pooling of appropriate fractions followed by removal of solvent as above yielded 157 mg of 1-carboxy-cyclopropane-[1,2]-buckministerfullerene t-butyl ester and 158 mg of bis{1-carboxy-cyclopropane}-[1,2]-[n,m]-buckminsterfullerene t-butyl ester (mixture of eight isomers).

Example 5

Synthesis of N-isoamyl-ethylurethane

In a 250 mL three-necked roundbottom 24/40 flask equipped with nitrogen inlet, dry ice bath, drying tube, pressure-equalizing addition funnel, and magnetic stirrer was added isoamylamine 3.935 g 45.1 mMol) and 5.35 gm (67.7 mMol) of dry redistilled pyridine. To this was added 40 mL of dry freshly redistilled dichloromethane. The solution was cooled to 0° C., and thereupon was added dropwise under nitrogen a solution of 4.89 gm (45.1 mMol) of ethyl chloroformate in 20 mL of dry redistilled dichloromethane. The addition was carried out over a 30-minute period. The mixture was then transferred to a separatory funnel, 100 mL of distilled water added, and the mixture then extracted with 3×100 ml portions of anhydrous ether. The combined ether extracts were washed with water, saturated sodium chloride, water, dried over anhydrous sodium sulfate, and concentrated on a Buchi rotary evaporator at 30° C. under mechanical pump vacuum (approximately 50 microns pressure). The slightly yellow oil was distilled in vacuo to yield 5.54 gm (77%) of purified material.

Example 6

Synthesis of N-nitroso-N-isoamyl-ethylurethane

In a 150 mL single-necked roundbottom 19/22 flask was placed 5.54 g (34.8 mMol) of N-isoamyl-ethylurethane in 55 mL of glacial acetic acid. This was cooled in an ice bath, and then 1.2 gm (five-fold excess) of sodium nitrite was added in small portions with stirring and cooling maintained over a twenty-minute period. The solution was allowed to stand at 6° C. for a one-hour period. The mixture was then transferred to separatory funnel, 100 mL of water added, and the solution was extracted with 2×50 mL portions of ether. The combined organic extracts were washed with water and 5% aqueous saturated sodium sulfate, and concentrated on a Buchi rotary evaporator at a temperature 30° C. under mechanical pump vacuum (approximately 50 microns pressure). The resultant yellow oil (5.34 g, 81.4%) was used without further purification owing to possible explosive hazards of distillation even at low pressure.

Example 7

Synthesis of 1-isopentylcyclopropa-[1,2]-buckminister-fullerene and bis-{1-isopentyl-cyclopropa}-[1,2]-[n,m]-buckministerfullerene library 10 mL of a 40% solution of potassium hydroxide in methanol and 10 mL of dry methanol were placed in an 125 mL Erlenmeyer flask equipped with a magnetic stirrer. To this was added 45 mL of dry ether and the resultant solution was cooled to 0° C. 500 mg of N-nitroso-N-isoamyl-ethylurethane was added dropwise over a 20-minute period, and the resulting mixture was allowed to remain at 0° C. for an additional 40-minute period. The strongly yellow-colored ether layer indicating the presence of the diazoalkane was decanted, and it was dried over KOH pellets. This solution was concentrated on a Buchi rotary evaporator at a temperature 30° C. under mechanical pump vacuum (approximately 50 microns pressure). The resultant yellow oil was used without further purification owing to possible explosive hazards of distillation even at low pressure. A 200 mg portion of this material was dissolved in a solution of 450 mg of $C_{60}$ in 200 mL of toluene. This solution was placed in a 500 mL three-necked roundbottom 24/40 flask equipped with nitrogen inlet, reflux condenser, and magnetic stirrer. The mixture was stirred at room temperature. After stirring for 3 hours, the solvent was removed under reduced pressure.

Example 8

Synthesis of a $C_{60}$ Monoadduct

To a solution of 72 mg (0.1 mmol) of buckminster-fullerene $C_{60}$ in toluene was added one equivalent of diazo compound A (as shown below) with stirring and cooling. The reaction mixture was allowed to warm to room temperature and then refluxed. After cooling, the solvent was evaporated and the residue separated by flash chromatography. Initial fractions contained unreacted $C_{60}$. Later fractions containing the product were combined to yield 47 mg of adduct B (6/6 and 6/5 isomers). NMR showed the presence of a p-substituted phenyl ring and a TBDMS group. Electrospray mass spectrometry (after tagging as described) showed the expected molecular ion peak.

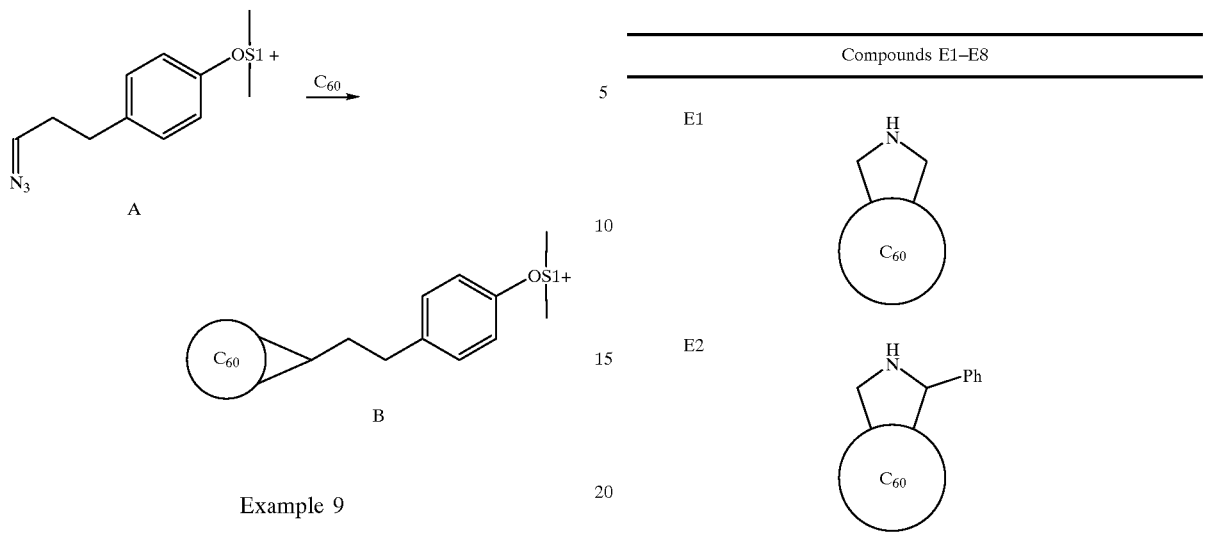

Example 9

Synthesis of a $C_{60}$ Monoadduct

A solution of 168 mg m-chloro-azide C (as shown below) (1.0 mmol) was added to a toluene solution of 360 mg (0.5 mmol) of $C_{60}$ and the reaction mixture was heated overnight at reflux. After the solution was cooled, the mixture was chromatographed to yield >300 mg recovered $C_{60}$ and 28 mg of mono-adduct D. The NMR of D showed a m-chloro group. The mass spectrum confirmed the expected molecular weight.

Example 10

Parallel Synthesis of Fullerene Library #1

Stoichiometrically controlled reactions with diazo compounds provide fullerenes with methano bridges [Wudl et al., *ACS Symp. Ser.* 1992, 481: 161–176]. Fullerene libraries of such compounds were prepared in multiwell plates. Each well of a 96-well Teflon plate was filled with 200 microliter samples dissolved in toluene of eight different fullerene monoadducts E1–E8 (shown below). These compounds were treated with one equivalent of 12 different diazo reagents F1–F12 (shown below), freshly prepared in separate flasks. The reagents were transferred to the multiwell plate under nitrogen by syringe.

The solutions were added at or below room temperature and then the plate was warmed to 50 degrees under nitrogen. After 1 hour, the plate was cooled and several drops of acetic acid were added to each well to quench any remaining diazo reagent. The entire plate was then heated under vacuum to remove all solvent. HPLC, TLC and electrospray MS of selected sample wells showed the desired products were formed in most cases. Unreacted $C_{60}$ was also found. Samples were further purified by HPLC

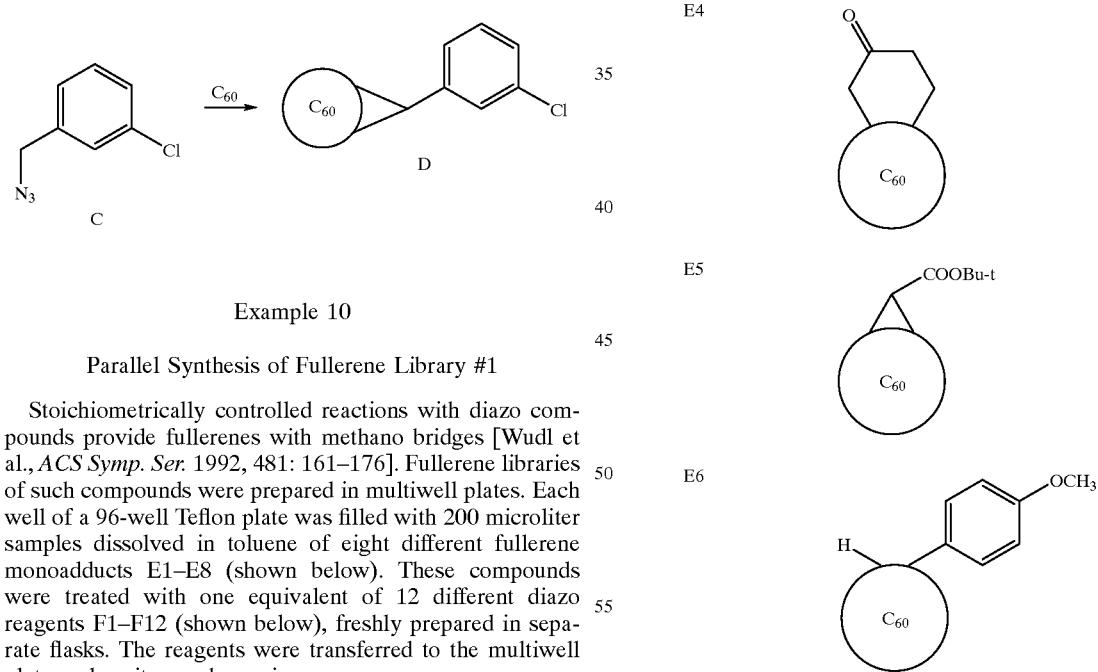

Compounds E1–E8

|     | -continued |
| --- | --- |
| E8  | 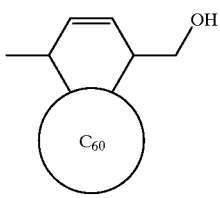 |

| Compounds F1–F12 | |
| --- | --- |
| F1  | CH$_2$N$_2$ |
| F2  | nC$_4$H$_6$N$_2$ |
| F3  | PhCHN$_2$ |
| F4  | PhC(CH$_3$)N$_2$ |
| F5  | Ph$_2$CN$_2$ |
| F6  | 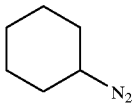 |
| F7  | 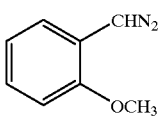 |
| F8  | 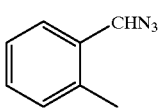 |
| F9  | 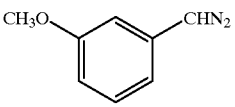 |
| F10 | 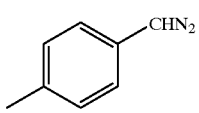 |
| F11 | 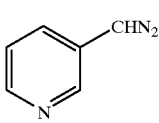 |
| F12 | 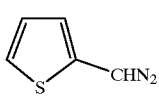 |

Example 11

Parallel Synthesis of Fullerene Library #2

Each well of a 96-well teflon plate was filled with 200 microliter samples dissolved in THF of eight different fullerene monoadducts G1–G8 (shown below). These compounds were treated with one equivalent of a THF solution of 12 different alkyl lithium reagents H1–H12 (shown below)(freshly prepared or purchased from Aldrich Chemical Co.). The reagents were transferred to the multiwell plate under nitrogen by syringe while the plate was cooled to below 0° C. After 1 hour, several drops of water were added to quench any remaining lithio reagent and the entire plate was then heated under vacuum to remove all solvent. HPLC, TLC and electrospray NS of selected sample wells showed the desired products were formed in most cases. Unreacted C$_{60}$ was also found. Samples were further purified by HPLC.

| Compounds G1–G8 | |
| --- | --- |
| G1  | 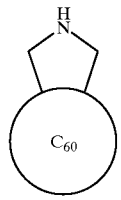 |
| G2  | 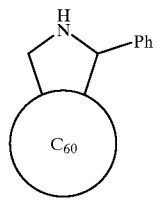 |
| G3  | 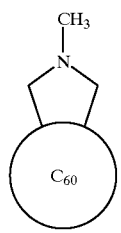 |
| G4  |  |
| G5  | 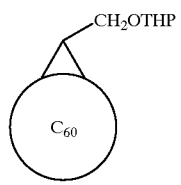 |
| G6  | 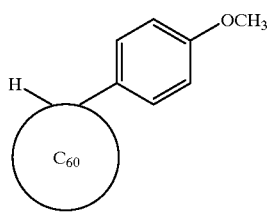 |

| | |
|---|---|
| G7 | 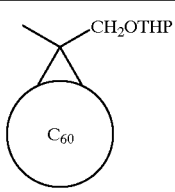 |
| G8 | 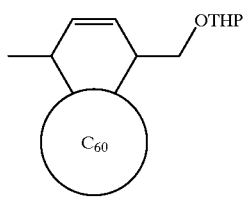 |

Compounds H1–H12

| | |
|---|---|
| H1 | CH₃Li |
| H2 | nC₄H₉Li |
| H3 | sC₄H₉Li |
| H4 | tC₄H₉Li |
| H5 | PhLi |
| H6 | 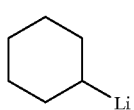 |
| H7 | 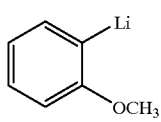 |
| H8 | 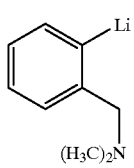 |
| H9 | 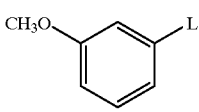 |
| H10 | 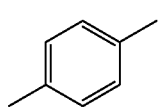 |
| H11 | 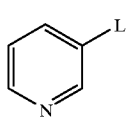 |
| H12 | 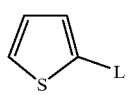 |

Example 12

Preparation of Multiply-substituted Fullerene Monolayers

In a Langmuir trough constructed according to Vodyanoy et al., *E. Anal. Symp.*, 208 (1980) [for general methodology of construction of monolayers see Grainger et al., *Biochem. Biophys. Acta* 1022:146–54 (1990)] equipped for the automatic quantification of surface pressure, surface area, and surface potential, was spread 10 µl of a solution in hexane (Burdick and Jackson Spectrograde, Glass Distilled) of bis-(k,n)-cyclopropyl-1-ethylamino-fullerene of concentration 1 micromolar and synthetic dioleylphosphatidylcholine (Avanti Polar Lipids, Inc.) at a concentration of 2 micromolar. The aqueous phase in these experiments was 10 mM Bis-Tris buffer, pH 7.8, containing 140 mM NaCl and 2 mM $CaCl_2$. In some studies the $Na^+$ was replaced with choline chloride, and in other studies the $Ca^{++}$ concentration was varied from 0.01–10 mM. The Langmuir trough had previously been cleaned with Spectrograde pentane, and the entire experimental apparatus was housed within a laminar flow hood to avoid contamination by particles or organic vapors. The surface area was contracted with a movable teflon film barrier connected to a stepping motor with a 7/0 polyamide suture. The surface pressure was measured by means of a non-wetted platinum plate dipping into the trough which is connected by a 9/0 polyamide suture to a Cahn recording microbalance (calibrated in a previous experiment with distilled water alone in the clean trough). The monolayer was formed when a constant relationship between the surface pressure and the surface area was maintained. Furthermore, the surface potential (measured with a $Po^{210}$ electrode held 100 micrometers above the monolayer, connected to a Keithely 610 A electrometer) became constant when the monolayer was maintained and no more hexane evaporated.

Example 13

Preparation of Multiply-substituted Fullerene Bilayers

Bilayers were formed from the above monolayers by dipping. The procedure of Vodyanoy et al., *Biochem. Biophys. Acta* 687:189–194 (1982) and Vodyanoy et al., *J. Coll. Inter. Sci.* 88:247–257 (1982) was used. This method involves raising a solution-filled bilayer chamber up through the monlayer using a micromanipulator (Narishige) and bringing it back down through the monolayer, completing the formation of the bilayer.

Formation of the bilayer was determined by measuring the current passing through the bilayer. A platinum electrode was located within the bilayer chamber, and a Ag/AbCl pipet electrode was located in the bathing medium of the bilayer chamber. The electrodes were hooked to a voltage clamp (Axoclamp II, Axon Instruments, Inc.) which measured the current as a function of voltage which passed through the bilayer. Typically, the current passing through such a multiply substituted fullerene bilayer is on the order of 50–400 picoamperes for a clamp voltage of 10 mV. Bilayers of this design are hydrostatically stabilized and therefore electrical and electro-optical measurements can be performed for many hours.

Example 14

Preparation of Multiply-substituted Fullerene Supported Bilayers

The method of Torchut, E. et al. was used [*Biophys. J.* 66:753–62 (1994)]. Bilayers were formed on the inner surface of a microporous template film of aluminum oxide deposited upon a gold plate electrode. The lipid monolayers are formed by absorption and fusion of phospholipid vesicles on alkylated oxide surfaces. Octadecyltrichlorosilane was used in the initial alkylation step. The aluminum oxide electrode was prepared by vacuum-depositing a 200 micrometer film aluminum (Alfa Inorganics, Inc. 99.999% pure pellets) at $2\times10^{-7}$ torr, and then admitting oxygen (Linde Gas Products research grade) to the chamber through an adjustable leak valve (Varian) such that the oxygen pressure reached $1\times10^{-3}$ torr over a 20 minute period. The electrode was then suspended in the monolayer trough, and surface pressure versus surface area was recorded during the deposition process.

Example 15

Release of an Odorant and Insect Pheromone from Multiply-substituted $C_{60}$

Citral is a commonly-employed odorant chemical used in perfumes. Citral also is pheromonal for some insects and repels other insects as well as canines. 12 mg of the library SPL-005, wherein the free amino group was protected with a trityl functionality, were placed in a thick glass tube equipped with an 18/9 male ball joint for connection to a high vacuum line and an appropriate ground glass high vacuum stopcock. The tube was evacuated to approximately $10^{-5}$ torr, and the residual oxygen was removed by heating to 50° C. for several hours. The tube was then cooled, and about 500 mg of citral (Fluka) distilled into the tube. The tube was then heated to 50° C. in the dark overnight. Under these conditions pressure was formed in the tube. The next day the stopcock was opened and the excess citral was removed in vacuo. The residue, which represents the SPL-005 adduct with citral together with a trace of polymerized aldehyde, was purified by flash chromatography.

The SPL-005 citral adduct was placed in a vial sealed with a silicone rubber septum closure. The air in the vial was then replaced with dry nitrogen. Samples of gas were withdrawn from the vial using a 1 cc gas-tight hamilton syringe. These gas-samples were then analyzed by gas chromatography/mass spectrometry for the specific presence of a peak corresponding in retention time to citral which showed the approximate mass corresponding to citral. The table below illustrates the results of this experiment.

| Time | Gas in Vial | GC/MS presence of citral |
| --- | --- | --- |
| day 1 | dry nitrogen | – |
| day 2 | dry nitrogen | ± |
| day 3 | dry nitrogen | ± |
| day 4 | nitrogen saturated water at 26° | ++++ |
| day 5 | nitrogen saturated water at 26° | ++++ |
| day 10 | nitrogen saturated water at 26° | ++++ |
| day 20 | nitrogen saturated water at 26° | +++ |

Upon opening the vial on day 25 there was a strong odor of citral associated with the preparation.

Example 16

$^3$He-NMR Analysis of Multiply-substituted $C_{60}$ Fullerenes $^3$He was introduced into fullerenes at 600° and 40,000 psi to obtain $^3$He-labeled fullerenes according to the method of Saunders et al., *J. Am. Chem. Soc.* (1994) 116:3621–22.

Figure 9:
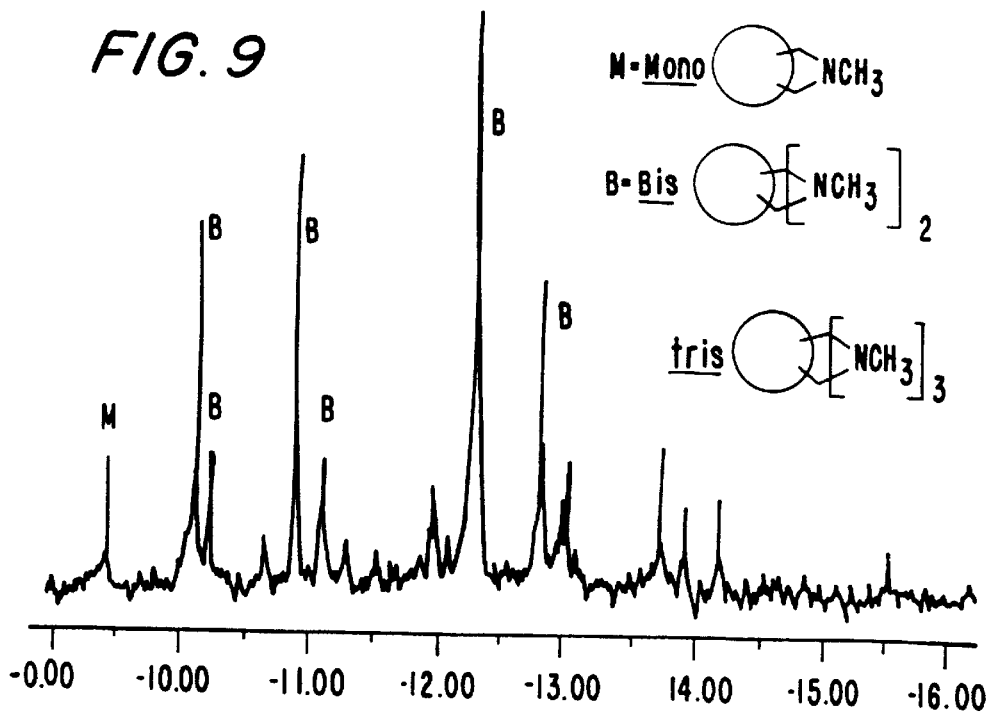
FIG. 9 is the $^3$He-NMR spectrum of a fullerene library prepared by addition of an excess of sarcosine and paraformaldehyde to $C_{60}$.
Figure 10:
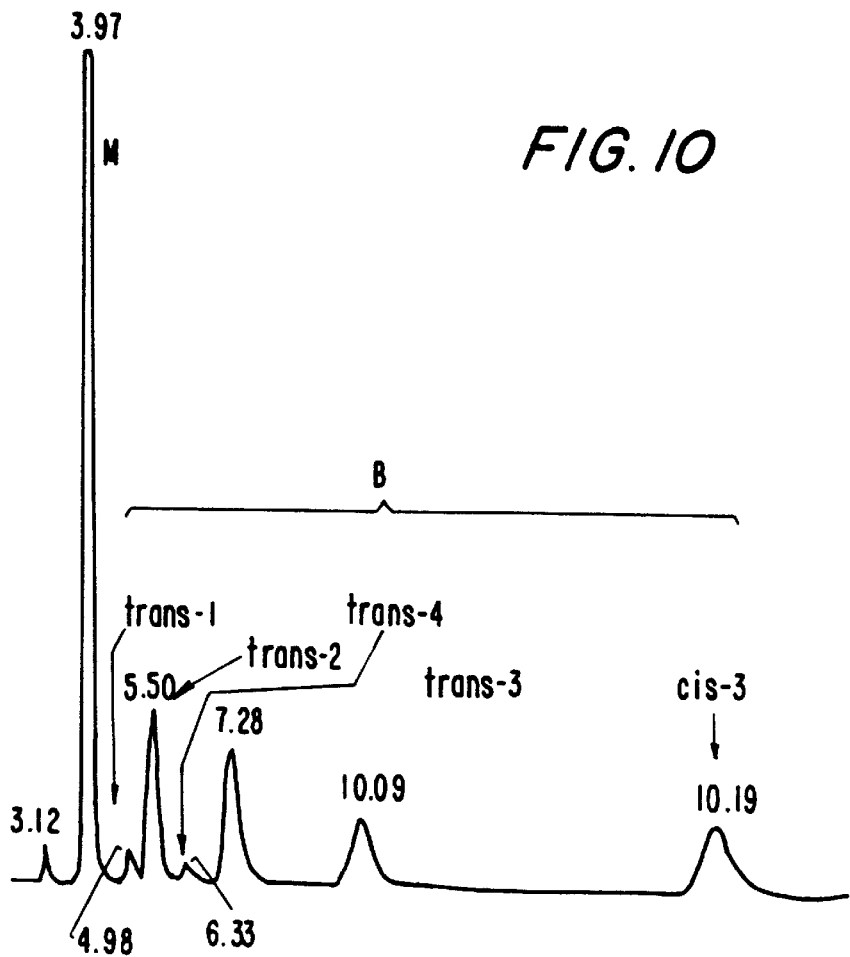
FIG. 10 is the HPLC separation of the fullerene library of FIG. 9.

A solution of 25 mg of $^3$He-labeled $C_{60}$ in toluene was treated with sarcosine and paraformaldehyde and refluxed for 3 hours. After removal of the toluene, the residue was checked by electrospray to show a library mixture of mostly mono- and bis- and some tris-substituted isomers. The mixture was dissolved in 4:1 mixture of 1-methyl-naphthalene $CD_2Cl_2$ containing about 1 mg chromium acetylacetonate. After a few hours of data collection at 381 MHZ (on a system that is 500 MHZ for $^1$H). The spectrum shown in FIG. 9 and the HPLC separation shown in FIG. 10 were obtained.

Collection and/or fractionation of HPLC peaks and confirmation of structure assignments by UV/Vis allows identification of which peak is which.

Example 17

$^3$HE-NMR Analysis of Multiply-substituted $C_{70}$ Fullerenes

Figure 11:
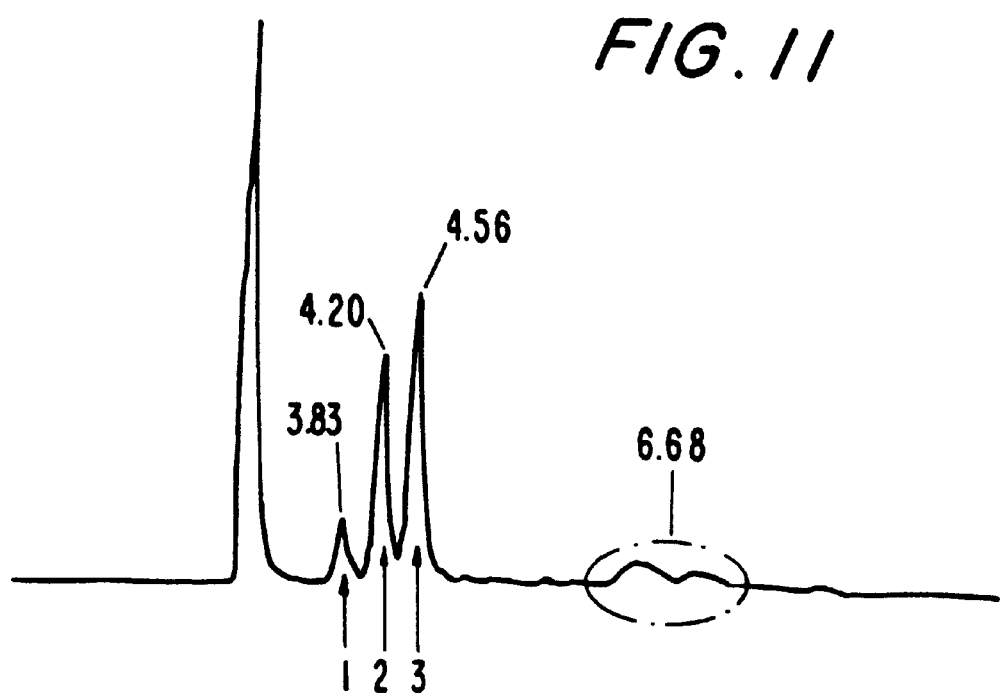
FIG. 11 is the HPLC separation of a fullerene library prepared by addition of an excess of sarcosine and paraformaldehyde to $C_{70}$.
Figure 12:
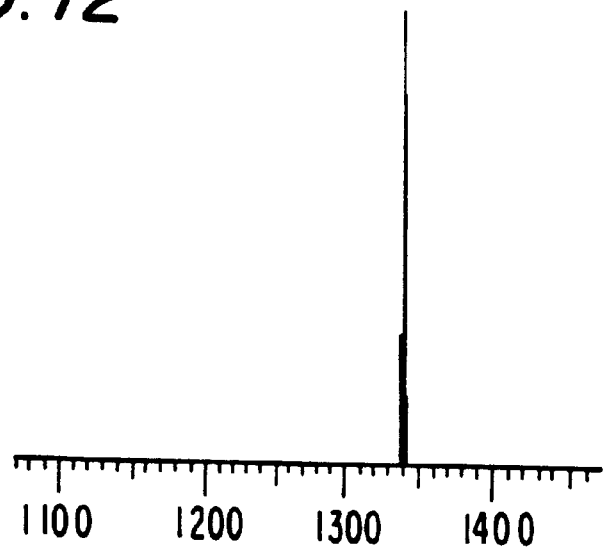
FIG. 12 is the electrospray mass spectrum of the fullerene library of FIG. 11.
Figure 13:
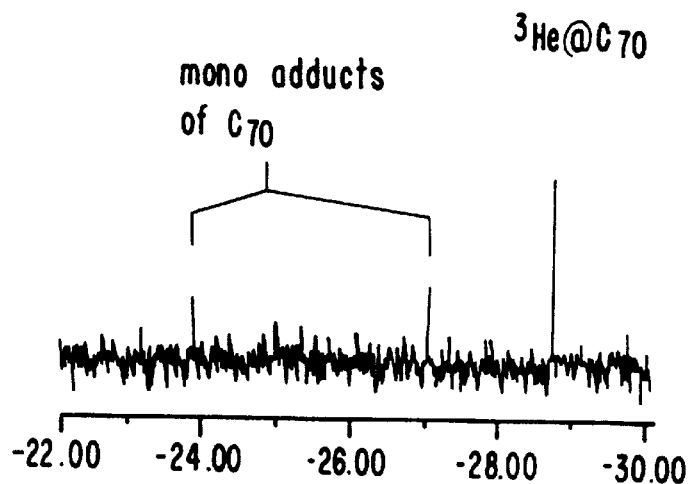
FIG. 13 is the $^3$He-NMR spectrum of the fullerene library of FIG. 11.

A fullerene library was prepared by reaction of $C_{70}$ in toluene with formaldehyde and sarcosine. Heating 5 hours at 110° gave a mixture of isomers 1, 2 and 3. The HPLC, showing the isomers as 3 separate peaks labeled 1, 2 and 3, is shown in FIG. 11. Each of these peaks gave the electrospray spectrum shown in FIG. 12. $^3$He NMR of the library was obtained under the sample instrument conditions described in Example 16, and the results are shown in FIG. 13.

Example 18

Electrospray Mass Spectrometric Analysis of Multiply-substituted Fullerenes

Figure 14:
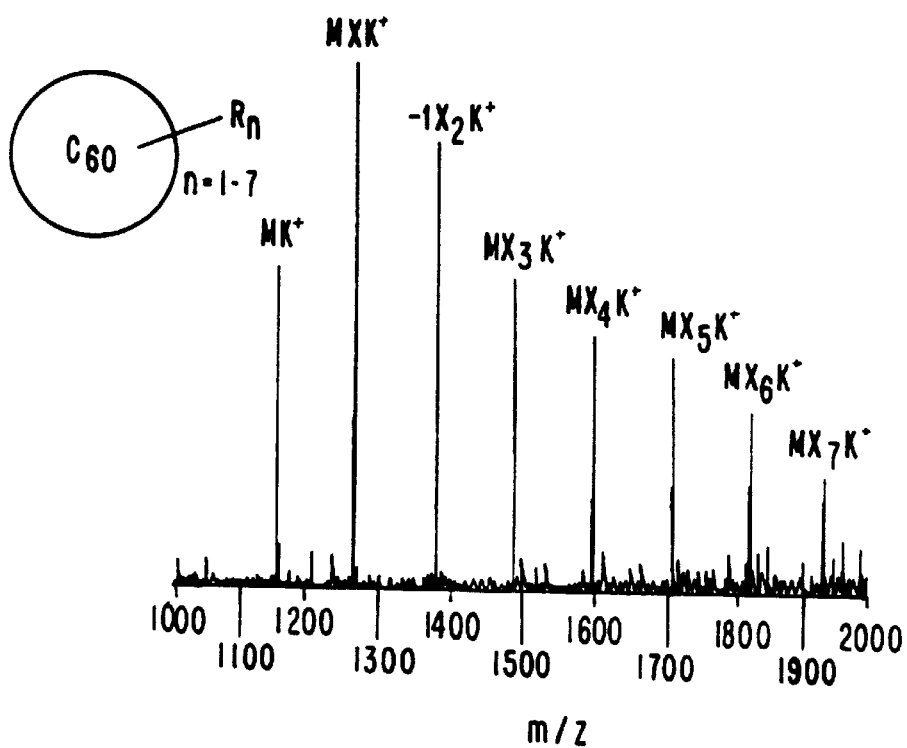
FIG. 14 is the electrospray mass spectrum of a fullerene library having seven functional groups added to $C_{60}$.

A fullerene library having seven functional groups added was prepared according to the method of the claimed invention. The library mixture was dissolved in 1:1 benzene-methanol, and infused into a Vestec Model 201 instrument at a flow rate of 5 $\mu$l/min. Data was collected with a Teknivent Vector One data system, processed and plotted. The spectrum obtained is shown in FIG. 14.

Example 19

Bead-based Peptide Library Coupling of Fullerenes

A small bis-Prato fullerene library is subjected to peptide library coupling as described by Houghten in *Nature* (1991) 354:84–86. A solution of the library is reacted with DCC and a BOC-protected amino acid, according to the method of Prato et al., *J. Org. Chem.* (1993) 58:5578–5580. The library construction is carried out by coupling mixtures of peptides and using the positional scanning technique for deconvolution.

In the following examples these libraries were examined for biological activity:

| Library | Structure |
|---------|-----------|
| SPL-004 | 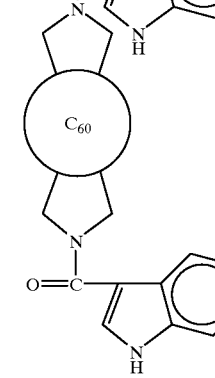 |
| SPL-005 | 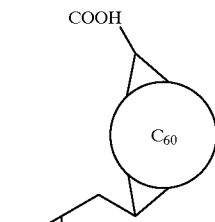 |
| SPL-006 | 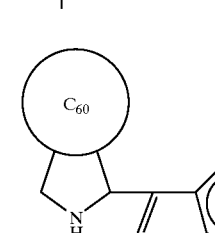 |
| SPL-007 | 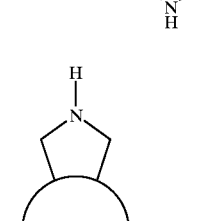 |

Example 20

Radioligand Association Assay for Sigma Receptor

Ten to twenty point radioligand binding assays in triplicate were performed using 4 nM [$^3$H]-haloperidol (specific activity=15 Ci/mmol, DuPont/New England Nuclear, Wilmington, Del.) or 0.4 nM [$^3$H]-DTG (specific activity= 39 Ci/mmol, DuPont/New England Nuclear) on crude or solubilized rat liver homogenates. Protein content of the crude homogenates ranged from 0.15 to 0.2 mg/ml as determined using the method described by Bradford, Anal. Biochem. 72:248–254 (1976). The concentration of displacing drug ranged between 0.2 nM and 100 uM in a final volume of 2.00 mL in buffer A (50 mM Tris(hydroxymethyl) aminoethane (Tris) HCl, 120 mM NaCl, 5 mM KCl, 5 mM ethylenediamine tetraacetic acid disodium salt (EDTA), 1 mM MgCl$_2$, pH 8.00). This buffer also contained 0.01 mg/mL o-phenanthroline (Aldrich, Milwaukee, Wis.), 0.1 mg/mL bacitracin (Sigma, St. Louis, Mo.), 0.05 mg/mL benzamidine (Calbiochem, LaJolla, Calif.), 0.005 mg/mL d-phenylalanine (Sigma), 0.05 mg/mL phenylmethylsulfonyl fluoride (PMSF, Sigma), and 0.2 mg/mL Soybean Trypsin Inhibitor (STI, Sigma). Non-specific binding was defined in the presence of 1 uM haloperidol. Spiperone (25 nM, Janssen, Belgium) was also added to inhibit association of [$^3$H]-haloperidol to dopamine D2 receptors which might be present. Incubation was carried out for one hour at room temperature after the addition of tissue. Samples were rapidly filtered through 0.1% polyethyleneimine (PEI, w/v, Sigma) soaked #32 glass fiber filters (Schleicher and Schuell, Keene, N.H.) on a 24-position cell harvester (Brandel, Gaithersburg, Md.). The filters were rapidly washed in the Brandel apparatus with two 2.0 mL aliquots of ice-cold 10 mM Tris buffer, pH 7.7. Filter zones containing tissue were punched from the filter strips into individual plastic scintillation minivials (7.0 mL capacity) each of which contained a 2.00 mL volume of Scinti Verse BD scintillation fluid (Fisher Scientific, Pittsburgh, Pa.). Radioactivity ([$^3$H]) was counted the following day at 40% efficiency on a Beckman LS 7500 scintillation counter. Binding data were analyzed by classical graphing techniques as well as by the iterative computer program LIGAND (Munson and Robard, 1980).

Example 21

Radioligand Association Assay for Dopamine D$_2$ Receptor

The dopamine D$_2$ binding activity of compounds was determined using a P$_2$ fraction (synaptosomal membranes) prepared from brains of male, Wistar rats. The D$_2$ assay employed a P$_2$ fraction from the striatum, the ligand [$^3$H]-spiperone at a concentration of 0.05 nM, and 1 mM haloperidol as a blank determinant. Protein content of the crude homogenates ranged from 0.15 to 0.2 mg/ml as determined using the method described by Bradford, Anal. Biochem. 72:248–254 (1976). Incubation was in buffer A (50 mM Tris (hydroxymethyl)aminoethane (Tris) HCl, 120 mM NaCl, 5 mM KCl, 5 mM ethylenediamine tetraacetic acid disodium salt (EDTA), 1 mM MgCl$_2$, pH 8.00), 0.01 mg/mL o-phenanthroline (Aldrich, Milwaukee, Wis.), 0.1 mg/mL bacitracin (Sigma, St. Louis, Mo.), 0.05 mg/mL benzamidine (Calbiochem, LaJolla, Calif.), 0.005 mg/mL d-phenylalanine (Sigma), 0.05 mg/mL phenylmethylsulfonyl fluoride (PMSF, Sigma), and 0.2 mg/mL Soybean Trypsin Inhibitor (STI, Sigma) for a 45-min period at 37° C. Samples were rapidly filtered through 0.1% polyethyleneimine (PEI, w/v, Sigma) soaked #32 glass fiber filters (Schleicher and Schuell, Keene, N.H.) on a 24-position cell harvester (Brandel, Gaithersburg, Md.). The filters were rapidly washed in the Brandel apparatus with two 2.0 mL aliquots of ice-cold 10 mM Tris buffer, pH 7.7. Filter zones containing tissue were punched from the filter strips into individual plastic scintillation minivials (7.0 mL capacity), each of which contained a 2.00 mL volume of Scinti Verse BD scintillation fluid (Fisher Scientific, Pittsburgh, Pa.). Radioactivity ([$^3$H]) was counted the following day at 40% efficiency on a Beckman LS 7500 scintillation counter. Binding data were analyzed by classical graphing techniques as well as by the iterative computer program LIGAND (Munson and Robard, 1980). Under these conditions, specific binding constituted 75% of total binding, and the IC$_{50}$ values for some known drugs were 0.32 nM for haloperidol and 92 nM for clozapine.

Example 22

Opiate Binding Assay

Crude membrane homogenates were prepared using a modification of the method described by G. W. Pasternak et al., *Mol. Pharmacol.*, 11:340–351 (1975). Rat brains frozen in liquid nitrogen were obtained from Taconic Farms, Inc. (Germaintown, N.Y.). The brains were thawed the cerebella removed, and the remaining tissue weighed. Each brain was individually homogenized in 40 ml Tris-HCl buffer (50 mM, pH 7.4, 4° C.) and centrifuged (Sorvall RC5C SA-600 16,000 rpm) for 10 minutes. The pellets were resuspended in fresh Tris-HCl buffer and incubated at 37° C. for 40 minutes. Following incubation, the suspensions were centrifuged as before, the resulting pellets resuspended in 100 volumes of Tris buffer, and the suspensions combined. Membrane suspensions were prepared and used in the same day. Protein content of the crude homogenates ranged from 0.15 to 0.2 mg/ml as determined using the method described by Bradford, *Anal. Biochem.* 72:248–254 (1976).

Binding assays were carried out in polypropylene tubes. Each tube contained 0.5 ml of membrane suspension, 8 nM [$^3$H]-DAGO (specific activity 36 Ci/mmole, 160,000 cpm), 0 0.08 mg/ml peptide mixture and Tris-HCl buffer in a total volume of 0.65 ml. Assay tubes were incubated for 60 minutes at 25° C. The reaction was terminated by filtration through GF-B filters. Samples were rapidly filtered through 0.1% polyethyleneimine (PEI, w/v, Sigma) soaked #32 glass fiber filters (Schleicher and Schuell, Keene, N.H.) on a 24-position cell harvester (Brandel, Gaithersburg, Md.). The filters are rapidly washed in the Brandel apparatus with two 2.0 mL aliquots of ice-cold 10 mM Tris buffer, pH 7.7. Filter zones containing tissue are punched from the filter strips into individual plastic scintillation minivials (7.0 mL capacity) each of which contained a 2.00 mL volume of Scinti Verse BD scintillation fluid (Fisher Scientific, Pittsburgh, Pa.). Radioactivity ([$^3$H]) is counted the following day at 40% efficiency on a Beckman LS 7500 scintillation counter. Binding data are analyzed by classical graphing techniques as well as by the iterative computer program LIGAND (Munson and Robard, 1980). Inter- and intra-assay variation standard curves were determined by incubation of [$^3$H]-DAGO in the presence of a range of concentrations of unlabeled DAGO (0.13–3900 nM). Competitive inhibition assays were performed as above using serial dilutions of the peptide mixture. IC$_{50}$ values (the concentration necessary to inhibit 50% of [$^3$H]-DAGO binding) were then calculated using the software were found to be consistent in three determinations.

Example 23

Assays of Binding to Adenosine A-2 Receptors

The potency of test compounds to compete with the ligand [H$^3$]-5'-N-ethyl-carboxamidoadenosine (NECA) for the adenosine A-2 receptors in rat brain membrane homogenates was measured in the binding assay. Crude tissue homogenates were prepared by the following general procedure. Frozen tissue was thawed and homogenized in a buffer containing 50 mM Tris, 120 EM NaCl, 5 mM KCl, 4 mM MgCl$_2$, and 5 mM KCl, pH 7.7. This tissue suspension is centrifuged at 30,000 rpm for 30 minutes. Following centrifugation, the supernatant was discarded and the resultant pellet was resuspended in the same buffer solution, and respun as previously described. The resultant pellet was suspended once more in the same buffer to give a final protein concentration of ca. 500 μg/mL, determined according to the Bradford dye-binding assay.

Incubation tubes, in triplicate, received 500 μL of [H$^3$]-NECA (8 nM final concentration; New England Nuclear), 500 μL of 1 μM cyclohexyladenosine (CHA), 500 μL of 100 mM MgCl$_2$, 500 μL of 1 IU/ml adenosine deaminase (Sigma), 500 μL of test compounds at various concentrations over the range of 10$^{-10}$ M to 10$^{-4}$ M diluted with assay buffer. Incubations were carried out at 25° C. for a 60 min-period. Samples were rapidly filtered through Schleicher and Schuell #32 glass filters presoaked with 0.1% polyethyleneimine, on a 24-position cell harvester. The filters were washed with 10 mM Tris buffer, pH 7.7, and then placed in 2 mL of scintillation fluid. Radioactivity was counted the following day at 40%–50% efficiency. Specific binding of [$^3$H]NECA was measured as the excess over blanks run in the presence of 100 μM 2-chloroadenosine. Specific binding to membranes was about 80% of the total bound. Displacement of [H$^3$]-NECA binding of 15% or more by a test compound was indicative of affinity for the adenosine A-2 site. The molar concentration of a compound which caused 50% inhibition of the binding of ligand was the IC$_{50}$. The following IC50 values were obtained:

| Library | IC$_{50}$ (nM) |
|---|---|
| SPL-004 | >6000 |
| SPL-005 | 349 |
| SPL-006 | >6000 |
| SPL-007 | 283 |

Example 24

Assays of Binding to 5-HT-1a and 5-HT-2 Receptors

Rat brain was homogenized and treated in a similar manner to above, except in ice-cold 0.25 M sucrose (1:30 w/v). The final pellet was resuspended in 50 mM Tris-citrate pH 7.4 at a concentration of 50 mg wet weight/mL and immediately used. For 5-HT-1a binding, membranes (300 mg protein) and 1.5 nM [$^3$H]-8-OH-DPAT were incubated in a 50 mM Tris citrate buffer pH 7.4 containing 7 mM MgCl and 0.5 mM EDTA. Incubations were carried out for a 10-min period at 37° C. in a final volume of 2.0 mL. Non-specific binding was determined in the presence of 3 mM buspirone and represented approximately 20% of specific [$^3$H]-8-OH-DPAT binding. For 5-HT-2 binding assays membranes (400–500 mg protein) and 1.0 nM [$^3$H]-ketanserin were incubated in 50 mM Tris HCl pH 7.4 at a final volume of 1.0 mL. Incubations were terminated after 15 min at 37° C. Non-specific binding was defined in the presence of 2 μM methysergide and represented approximately 25% of specific [$^3$H]-ketanserin binding. For each binding assay, bound ligand was separated from free by vacuum filtration over GF/B filters on a Brandel cell harvester. The filters were washed twice for 10 s with incubation buffer and the bound radioactivity determined by liquid scintillation counting.

Example 25

Assays of Binding to 5-HT-1b Receptor

Rat striatal tissue was homogenized as above. The pellet was resuspended in a binding buffer (25 mM TRIS-HCl, pH 8.0) for use in the binding assays. All binding assays were performed at 22° C. These washing conditions yielded optimal specific binding. For displacements, membrane pellets were brought up to 500 vol in binding buffer. Drugs were added to polypropylene assay tubes, followed by membrane suspension and then [$^{125}$I](−)-iodocyanopindolol (final concentration about 30 pM), and these were incubated for 45 min at 22° C. Binding assays were terminated by rapid filtration through GF/C glass fiber filter strips. Tubes and filters were washed three times within a 20-second period with 4 mL of TRIS-HCl, pH 8.0, at 22° C. containing 30 mM racemic propranolol and 30 mM phentolamine, to reduce nonspecific binding of [$^{125}$I](−)-iodocyanopindolol. Total binding is the binding in the absence of competing drug, and nonspecific binding is the binding in the presence of 10 μM nonradioactive 5-HT.

Example 26

Assays of Binding to 5-HT-3 Receptors

Rat brain was homogenized as in the 5-HT-1a assay above. The pellet is resuspended in 50 mM Tris-HCl pH 7.6 at a concentration of 50 mg wet weight/ml and was immediately used. The binding assay for [$^3$H]-zacopride was performed in triplicate at 37° C. for 30 min. Incubations were contained 5 mM Tris-Cl, pH 8.5 (buffer B), 150 mM NaCl, 0.15–1 mg of membrane protein, and 1 nM [$^3$H]-zacopride in a total volume of 600 μL. Incubations were initiated by the addition of membranes and terminated, at the times indicated, by the addition of 10 volumes of ice cold buffer B followed by rapid vacuum filtration on a Brandel Cell Harvester. Bound ligand was recovered on Whatman GF/C filters (pretreated with 0.1% polyethyleneimine) that were washed four times with 5 ml of buffer B at 4° C. The amount of [$^3$H]zacopride bound is measured by liquid scintillation spectrometry. Total specific binding is defined as that displaced by 20 mM zacopride. Non-specific binding was calculated as the difference between total binding and total specific binding. 5-HT-3 specific binding was defined as that displaced by 500 nM ICS-205-930 (3α-tropanyl-1H-indole-3-carboxylate).

Example 27

Assays of Binding to α-1-Receptor Subtypes

α-1-Adrenoceptors were labelled with [$^3$H]-prazosin. Tissue pellets were prepared as in the 5-HT-1a assay and were resuspended by homogenization in 50mM TRIS HCl buffer containing 1 mM EDTA (pH 7.4), incubated for a 10-minute period at 37° C. and washed once more in ice-cold buffer. Where indicated, membrane suspensions obtained after the first centrifugation step were preincubated with or without 10 mM chloreoethylclonidine for a 30-minute period at 37° C. and subsequently washed twice. Incubations were carried out in triplicate using 0.2 nM [$^3$H]-prazosin, and multiple concentrations of competing drugs, in a final volume of 1.0 mL. The incubation buffer consisted of TRIS HCl 50 mM, EDTA 1 mM pH 7.4). Incubations were terminated after a 45-minute period by rapid filtration through Whatman GF/C filters by using a Brandel cell harvester. The filters were washed with 3×5 ml portions of ice-cold incubation buffer and the radioactivity retained on the filters was determined by liquid scintillation counting. Phentolamine, in a concentration sufficient to inhibit association to both α-1-adrenoceptor subtypes (10 mM), was used to define nonspecific binding (about 25% of total binding).

Example 28

Assays of Binding to the Dopamine Transporter

Rat striatal tissue was homogenized as in the 5-HT-1a assay. The pellet was re-homogenized in 1000 volumes (original tissue wet weight) of the buffer. The assay mixture contains [$^3$H]-GBR 12935 at a final concentration of 1 nM and varying concentrations of the appropriate test compound. Since this radioligand is capable of associating with very high affinity to sigma receptors, 100 nM pentazocine was included to block these sigma sites. The incubations were carried out for a 60-min period at 20° C. and were terminated by rapid filtration of the incubation mixture and measurement of radioactivity as described above.

Example 29

Assays of Binding to the 5-HT Transporter

Rat striatal tissue was homogenized as described above and was resuspended in binding buffer (25 mM TRIS-HCl, pH 7.4, containing 120 mM NaCl and 5 mM KCl). All binding assays were performed at 22° C. For displacements, membrane pellets were brought up to 500 vol in binding buffer. Drugs were added to polypropylene assay tubes, followed by membrane suspension, [$^3$H]-paroxetine (0.2 nM in the case of displacements), buffer, and buffer and/or displacing drug. (±)-Fluoxetine (1 μM) was used as the displacing drug to define nonspecific binding. After a 60-minute period, incubations were terminated by filtration and radioactivity quantified as above.

Example 30

Tachykinin Antagonism Assay

Male albino guinea pigs weighing 200 to 500 grams were sacrificed by cervical dislocation. The ilea were then quickly removed from the guinea pigs-and placed in a modified Tyrode solution, a solution which is known to those skilled in the art, containing one-half of the usual amount of magnesium ions.

Segments of ileum about 2 cm long were then cut and mounted in a 10 mL tissue bath containing the modified Tyrode solution. The solution was maintained at 37 degrees C. and aerated with a gaseous mixture of 95% oxygen and 5% carbon dioxide. Data for a control tachykinin dose response curve was obtained by experimentally adjusting the dose of the tachykinin being injected into the tissue bath, in a manner known by those skilled in the art.

Solutions or suspensions containing an initial concentration (1 nanomolar) of a test compound in modified Tyrode solution ("test solutions/suspensions") were then separately substituted for the control bath solution. Each test solution/suspension was then kept in constant contact with the ileum-tissue, except for brief periods to drain the bath in preparation for rinsing with fresh test solution/suspension. A second tachykinin dose response curve was then generated for tachykinin in the presence of a test compound.

A dose ratio of $ED_{50}$ doses was then calculated from the results of each test in a manner known by those of skill in the art. A test compound was determined to be "active" if the initial concentration used yielded at least a two-fold shift (dose ratio greater than or equal to 2) in the dose response curve for 10 tachykinin. An estimated $pA_2$ value (a statistical constant which is a common measure of expressing the potency of a particular drug as an antagonist) was reported for "active" compounds under the assumption that the slope of the Schild plot does not deviate significantly from −1.0. If the initial concentration of test compound yielded at least a five-fold shift (dose ratio greater than or equal to 5) in the dose response curve for tachykinin, then varying concentrations of the test compound were assayed, and a $pA_2$ value for that compound was calculated by Schild plot calculations, as described by H. O. Schild, in *Brit. J. Pharm.*, 2:189 (1947). The higher the value calculated for the $pA_2$, the more potent a particular compound is as a tachykinin antagonist. The results of this tachykinin antagonism assay are presented in the table below.

| Library Number | POTENCY IN GUINEA PIG ILEUM ($pA_2$) |
| --- | --- |
| SPL-004 | 7.4 |
| SPL-005 | 5.3 |
| SPL-006 | 6.2 |
| SPL-007 | 6.7 |

Example 31

Glutamate Receptor Subtype Binding Assay

Rat cortical membranes were prepared as above but in the following buffer: 50 mM Tris-malate, pH 7.4 containing 0.5 mM EDTA, and 1 mM $MgSO_4$. In addition, the membranes were washed two additional times to remove endogenous amino acids. The general method involved adding the radio-ligand (12.5 nM L-[$H^3$]-glutamate; 0.5 nM [$H^3$]-kainate or 10 nM ($H^3$)-AMPA) to the appropriate concentration of the test compound and initiating the assay by the addition of ice cold cortical membranes (0.2–0.45 mg). In some studies [$H^3$]-CGS19755 was used in place of glutamate [Murphy et al. *Brit. J. Pharmacol.*, 95:932–938 (1988)]. The binding assays were performed in glass tubes with the total volume adjusted to 5.0 mL. Additions of test compounds were made in 50 mM Tris/acetate, pH 7.4 and incubations were carried out at 0–4° C. The incubation time for the NMDA and the AMPA binding assays was 10 minutes, for the kainate binding assay 60 minutes and for the sodium-dependent glutamate binding assay 15 minutes. The AMPA binding assay contained 100 nM KSCN (Nielson et al. *Eur. J. Med. Chem.* 21:433–437 (1986)] and the sodium-dependent glutamate binding assay contained 150 mM sodium acetate in addition to the previously described reagents. To terminate the incubation, tubes were rapidly filtered through S and S glass fiber filters in a Brandel cell homogenizer. Filters were washed three times with 3 ml of ice-cold buffer. The filters were placed in scintillation fluid for 48 hours and counted as above. Nonspecific binding was operationally defined as the residual binding in the presence of either excess unlabeled L-glutamate (200 mM), kainate (0.01 mM), or NMDA (0.5 mM), and was 15–25% of the total binding in the NMDA binding assay, 20–30% in the AMPA binding assay, 20–30% in the kainate binding assay and 10–12% in the sodium-dependent binding assay. The following $IC_{50}$ values were obtained:

| Library | $IC_{50}$ (nM) |
| --- | --- |
| SPL-004 | 572 |
| SPL-005 | 340 |
| SPL-006 | 128 |
| SPL-007 | 483 |

Example 32

Effect of Multiply-substituted Fullerenes as Neurotransmitter Antagonists in Functional Physiological Assay Male albino guinea pigs weighing 200 to 500 grams were sacrificed by cervical dislocation. The ilea were then quickly removed from the guinea pigs and placed in a modified Ringers solution, which consists of 119 mmol/l of NaCl; 2.2 mmol/l of $CaCl_2$; 1.6 mmol/l to $KH_2PO_4$; 10 mmol/l of glucose; 4.8 mmol/l of KCl; 0.8 mmol/l of $MgSO_4$, 25 mmol/l of $NaHCO_3$, and 1 mM/l of sodium pyruvate.

The ileum was washed, and the longitudinal muscle was carefully removed according to a procedure well known to those skilled in the art. Segments of longitudinal muscle of the ileum of about 1.4 cm in length were then cut and mounted in a 10 mL tissue bath containing the modified Ringers solution. The solution was maintained at 37° C. and aerated with a gaseous mixture of 95% oxygen and 5% carbon dioxide. Data for a control neurotransmitter dose response curve was then obtained by experimentally adjusting the dose of the neurotransmitter being injected into the tissue bath, in a manner known by those of skill in the art. Displacement was recorded by means of a Grass FT10 force transducer, hooked to a multichannel polygraphic chart recorder (Grass Instruments).

Solutions or suspensions containing an initial concentration (1 nanomolar) of a test compound in modified Ringers solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second neurotransmitter dose response curve was then generated for neurotransmitter in the presence of a test compound.

A dose ratio of $ED_{50}$ doses was then calculated from the results of each test in a manner known by those of ordinary skill in the art. A test compound was determined to be "active" if the initial concentration used yielded at least a two-fold shift (dose ratio greater than or equal to 2) in the dose response curve for 10 neurotransmitter. An estimated $pA_2$ value (a statistical constant which is a common measure of expressing the potency of a particular drug as an antagonist) was reported for "active" compounds under the assumption that the slope of the Schild plot does not deviate significantly from −1.0. If the initial concentration of test compound yielded at least a five-fold shift (dose ratio greater than or equal to 5) in the dose response curve for neurotransmitter, then varying concentrations of the test compound were assayed, and a $pA_2$ value for that compound was calculated by Schild plot calculations, as described by H. O. Schild in *Brit. J. Pharm.*, 2:189 (1947). The higher the value calculated for the $pA_2$, the more potent a particular compound is as a neurotransmitter antagonist.

The results of the neurotransmitter antagonism assays are presented below.

| Example Number | POTENCY IN GUINEA PIG ILEUM ($pA_2$) |
|---|---|
| Neurotransmitter: Acetylcholine | |
| SPL 004 | 6.4 |
| SPL 006 | 5.3 |
| SPL 005 | 5.6 |
| SPL 007 | 4.8 |
| Neurotransmitter: Cholecystokinin (indirect) | |
| SPL 004 | NT |
| SPL 006 | NT |
| SPL 005 | 5.4 |
| SPL 007 | NT |
| Neurotransmitter: Serotonin (5-HT) | |
| SPL 004 | 7.2 |
| SPL 005 | 7.1 |
| SPL 006 | 5.2 |
| SPL 007 | NT |

Example 33

Investigation of the Inhibition of Contraction by Fullerene Libraries Which Is Induced with Aconists Potent at Receptors for Serotonin, Angiotensin, Noradrenaline and Adrenaline Rabbits of both sexes were stunned by a blow to the neck and exsanguinated or, where appropriate, anaesthetized with Nembutal (about 60–80 mg/kg i.v.) and sacrificed by opening the thorax. The thoracic aorta was removed, freed from attached connective tissue and divided into ring segments 1.5 mm wide, and the segments were introduced individually, under an initial load of about 3.5 g, into 10 ml organ baths containing 95%$O_2$-5% $CO_2$-gassed Krebs-Ringer solution thermostatically controlled at 37 degrees C. and having the following composition: 119 mmol/l of NaCl; 2.5 mmol/l of $CaCl_2$; 1.2 mmol/l to $KH_2PO_4$; 10 mmol/l of glucose; 4.8 mmol/l of KCl; 1.4 mmol/l of $MgSO_4$ and 25 mmol/l of $NaHCO_3$.

The contractions were recorded isometrically by Grass FT10 displacement transducers hooked to a multi-pen recorder (Grass). The agonist dose/effect curves were plotted hourly. For each dose/effect curve, 3 or 4 individual concentrations were applied to the baths at intervals of 4 minutes. The dose/effect curve and subsequent wash-out cycles (16 times for about 5 sec/min each with the above nutrient solution) were followed by a 28-minute resting or incubation phase, within which the contractions as a rule reach the starting value again. The level of the dose/effect curve in the normal case was used as a reference parameter for evaluating the test substance which was to be investigated in subsequent passes the subsequent dose/effect curve was applied to the baths at the start of the incubation time in a dosage which increased each time. Each aortic ring was always stimulated with the same agonist over the entire day.

The $pA_2$ was calculated according to the methods described in the previous example. The compounds according to the invention inhibit serotonin and noradrenaline-induced contraction of the isolated rabbit aorta as a function of the dose, but not angiotensin-induced contraction as shown below.

Inhibition of Vascular Contraction on Isolated Aortic Rings of Rabbits in vitro

| | $pA_2$ against contractions induced by: |
|---|---|
| Noradrenalin | |
| SPL 004 | <4 |
| SPL 006 | 6.3 |
| SPL 005 | <4 |
| SPL 007 | <4 |
| Serotonin | |
| SPL 004 | 7.84 |
| SPL 006 | 6.1 |
| SPL 005 | 5.2 |
| SPL 007 | NT |
| Angiotensin II | |
| SPL 004 | <4 (inactive) |
| SPL 006 | <4 |
| SPL 005 | <4 |
| SPL 007 | NT |

Example 34

Transdermal Delivery System for Fullerenes

In the case of largely water soluble drugs, such as highly substituted fullerenes, transdermal delivery can be achieved by admixing an appropriate amount of oil surfactant, such as polyethoxylated castor oil, with an appropriate amount of a pharmaceutical grade co-solubilizer alcohol to obtain a non-aqueous continuous phase.

After the oil surfactant and co-solubilizer alcohol solution is sufficiently mixed, the fullerene medicament is dissolved in an appropriate amount of distilled water. The water and water soluble drug solution are slowly added to the non-aqueous continuous phase with agitation and a slight amount of heat; however, the heat is never to exceed 40° C. The resulting mixture is cooled to provide a visibly clear, oil-continuous solution that is suitable for transdermal delivery into selected areas of the body.

Specifically, one ml concentration 2.5 mg/ml of a bis-(Prato)-fullerene mixture containing 2, 3, and 4 substituents, in which these substituents are glutamate sidechains, in an isotonic sodium chloride solution is added to an 80 ml solution of equal amounts of 99% alcohol and an ethoxylated oil while stirring until a clear yellow aqueous solution appears. Thereafter, q.s. to 100 ml with either 20 ml of ethoxylated oil and alcohol solution or 20 ml of sodium chloride, depending on the desired viscosity.

Example 35

Catalysis of Methane Conversion Utilizing Multiply-Substituted Fullerenes

A 5 ml tubular high-temperature flow reactor is packed with a library of multiply-substituted $C_{60}$ and activated with carbon dioxide and gaseous material passed through at 600°–1000° C. at 500–1000 psi for two hours. The fullerenes lower the methane conversion temperature by approximately 250° C.

Having thus described exemplary embodiments of the present invention, it should be noted by those skilled in the art that the within disclosures are exemplary only and that various modifications may be made within the scope of the present invention. Accordingly, the present invention is not limited to the specific embodiments as illustrated herein, but is only limited by the following claims along with their full scope of equivalents.

What is claimed is:

1. A method for the simultaneous synthesis of a multiplicity of different multiply-substituted fullerenes having the formula:

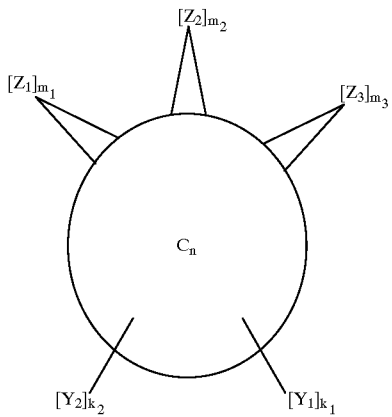

wherein:

$Z_1$, $Z_2$ and $Z_3$ are absent or present, provided that at least one is present, and are independently selected from the group consisting of $-CR_1R_2-$, $-CR_1R_2-CR_3R_4-$, $-NR_1-$, $-O-CR_1R_2-$, $-S-CR_1R_2-$, $-NR_1-CR_2R_3-$, $-R_1R_2C-NR_3-CR_4R_5-$, $-R_1C=N-CR_2R_3-$, $-R_1R_2C-NR_3-NR_4-$, $-R_1R_2C-NR_3-O-$, $-N=NR_1-$, $-N=N-NR_1-$, $-N=N-CR_1R_2-$, $-O-NR_1-O-$, $-R_1R_2C-O-CR_3R_4-$, $-R_1R_2C-O-NR_3-$, $-R_1C=N-NR_2-$, $-R_1C=N-O-$, $-R_1N-NR_2-NR_3-$, $-R_1N-NR_2-O-$, $-CR_1R_2-CR_3R_4-CR_5R_6-$, $-CR_1R_2-CR_3=CR_4-$, $-CR_1R_2-CR_3R_4-CR_5CR_6-CR_7R_8-$, $-CR_1=R_2-CR_3R_4-CR_5R_6-$, $-CR_1R_2-CR_3=CR_4-CR_5R_6-$, $-CR_1=CR_2-CR_3=CR_4-$ and $-CR_1R_2-CR_3=C=CR_4-$ such that $Z_1$, and $Z_2$ and $Z_3$ are each attached to the carbon skeleton of the fullerene structure by two single bonds selected from the group consisting of a carbon-carbon bond, a carbon-oxygen bond, a carbon-sulfur bond, and a carbon-nitrogen bond, the unsatisfied valences of each Z moiety being the location of those bonds;

$R_1$, $R_2$, $R_3$, $R_4$, $R_5$, $R_6$, $R_7$ and $R_8$ are the same or different and are selected form the group consisting of hydrogen, oxygen, lower alkyl, higher alkyl, cycloalkyl, alkenyl, alkynyl, alkoxy, carboxylic acids, carboxylic esters, alkytlthio, thioalkyl, aryl, aryloxy, aralkyl, primary amine, secondary amine, amino acid side chains, and heterocycles, such that C together with any two R groups bonded thereto forms an oxo or thioxo group, hydrocarbon ring or heterocycle;

$Y_1$ and $Y_2$ are absent or present, providing that at least one is present, and are selected from the group consisting of hydrogen, lower alkyl, higher alkyl, cycloalkyl, alkenyl, alkynyl, alkoxy, alkylthio, thioalkyl, aryl, aryloxy, aralkyl, primary amine, secondary amine, amino acid side chains, and heterocycles;

$20<n<240$;

$(k_1+k_2)$ is 1 to n; and $(m_1+m_2+m_3)$ is 1 to n/2, with the limitation that $2(m_1+m_2+m_3)+(k_1+k_2) \leq n$;

or a salt or addition compound thereof;

said method comprising the steps of:
(a) reacting fullerenes of the formula $C_n$, wherein $20<n<240$, with a first compound containing the moiety Z, or the moiety Y; and
(b) reacting said fullerenes with a second compound containing the other of the moiety $Z_1$ or the moiety Y.

* * * * *